(12) United States Patent
Chin

(10) Patent No.: US 10,722,722 B2
(45) Date of Patent: *Jul. 28, 2020

(54) MITIGATING FALSE MESSAGING IN LEADLESS DUAL-CHAMBER PACING SYSTEMS AND OTHER IMD SYSTEMS

(71) Applicant: Pacesetter, Inc., Santa Clara, CA (US)

(72) Inventor: Donald Chin, Palo Alto, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/204,049

(22) Filed: Nov. 29, 2018

(65) Prior Publication Data
US 2019/0099607 A1    Apr. 4, 2019

Related U.S. Application Data

(63) Continuation of application No. 15/423,409, filed on Feb. 2, 2017, now Pat. No. 10,173,068.

(51) Int. Cl.
| | |
|---|---|
| *A61N 1/372* | (2006.01) |
| *A61N 1/02* | (2006.01) |
| *A61N 1/362* | (2006.01) |
| *A61N 1/375* | (2006.01) |
| *H04L 1/00* | (2006.01) |
| *H04L 1/20* | (2006.01) |
| *G06F 11/10* | (2006.01) |
| *H04L 1/18* | (2006.01) |

(52) U.S. Cl.
CPC ......... *A61N 1/37252* (2013.01); *A61N 1/025* (2013.01); *A61N 1/362* (2013.01); *A61N 1/3756* (2013.01); *A61N 1/37205* (2013.01); *G06F 11/1004* (2013.01); *H04L 1/0061* (2013.01); *H04L 1/20* (2013.01); *H04L 1/201* (2013.01); *H04L 1/1812* (2013.01)

(58) Field of Classification Search
CPC .......... A61B 5/00; A61N 1/375; A61N 1/372; A61N 1/37; A61N 3/37252
See application file for complete search history.

(56) References Cited

U.S. PATENT DOCUMENTS

| | | |
|---|---|---|
| 6,427,088 B1 | 7/2002 | Bowman |
| 6,443,891 B1 | 9/2002 | Grevious |
| 6,535,766 B1 | 3/2003 | Thompson et al. |
| 7,218,969 B2 | 5/2007 | Yallapureddy |
| 8,509,911 B2 | 8/2013 | Li |

(Continued)

OTHER PUBLICATIONS

Non-final Office Action dated Dec. 29, 2017; Related U.S. Appl. No. 15/423,404.

(Continued)

*Primary Examiner* — Albert K Wong
(74) *Attorney, Agent, or Firm* — Vierra Magen Marcus LLP

(57) ABSTRACT

Implantable medical devices (IMDs), and methods for use therewith, reduce how often an IMD accepts false messages. Such a method can include receiving a message and performing error detection and correction on the message. Such a method can also include determining a quality measure indicative of a quality of the message and/or a quality of a channel over which the message was received, and determining whether to reject the message based on the quality measure.

20 Claims, 10 Drawing Sheets

(56) References Cited

U.S. PATENT DOCUMENTS

| | | | |
|---|---|---|---|
| 8,607,305 | B2 | 12/2013 | Neystadt |
| 9,168,380 | B1 * | 10/2015 | Greenhut et al. |
| 10,173,068 | B2 * | 1/2019 | Chin .................. G06F 11/1004 |
| 2002/0045920 | A1 | 4/2002 | Thompson |
| 2005/0283198 | A1 | 12/2005 | Haubrich |
| 2008/0027501 | A1 | 1/2008 | Haubrich et al. |
| 2011/0082379 | A1 | 4/2011 | Sullivan |
| 2015/0147073 | A1 | 5/2015 | Nonaka |
| 2016/0038747 | A1 | 2/2016 | Maile |
| 2016/0121127 | A1 | 5/2016 | Klimovitch et al. |
| 2016/0121128 | A1 | 5/2016 | Fishier et al. |
| 2016/0121129 | A1 | 5/2016 | Persson et al. |
| 2016/0250483 | A1 | 9/2016 | Klimovitch et al. |
| 2017/0054516 | A1 | 2/2017 | Schmidt |
| 2017/0132120 | A1 | 5/2017 | Salameh |
| 2017/0216610 | A1 | 8/2017 | Yoder |
| 2017/0257761 | A1 | 9/2017 | Rodriquez |
| 2017/0317518 | A1 | 11/2017 | Olson |
| 2018/0176293 | A1 | 6/2018 | Ding et al. |
| 2018/0214703 | A1 | 8/2018 | Chin |
| 2018/0214704 | A1 | 8/2018 | Chin |

OTHER PUBLICATIONS

Restriction Requirement dated Jul. 10, 2018; Parent U.S. Appl. No. 15/423,409.

Response to Election/Restriction Requirement dated Jul. 12, 2018; Parent U.S. Appl. No. 15/423,409.

Notice of Allowance dated Sep. 19, 2018; Parent U.S. Appl. No. 15/423,409.

* cited by examiner

ID DUAL-CHAMBER PACING

MITIGATING FALSE MESSAGING IN LEADLESS DUAL-CHAMBER PACING SYSTEMS AND OTHER IMD SYSTEMS

PRIORITY CLAIM

This application is a continuation of, and claims priority to, U.S. patent application Ser. No. 15/423,409, filed Feb. 2, 2017, published as US 2018/0214704 on Aug. 2, 2018 and issued as U.S. Pat. No. 10,173,068 on Jan. 8, 2019, which is incorporated herein by reference.

FIELD OF TECHNOLOGY

Embodiments described herein generally relate to methods and systems for communication between implantable medical devices, or communicating between a non-implantable device and an implantable medical device.

BACKGROUND

Implantable medical devices and systems often rely on proper communications to operate correctly. For example, in a dual chamber pacemaker system, implant-to-implant (i2i) communications are critical for proper synchronization and operation of the system. However, noise may cause one or more devices of such a system to falsely detect an i2i message and inappropriately respond thereto. For a more specific example, noise may cause a ventricular leadless pacemaker (LP) to falsely detect a message from an atrial LP, which then could trigger the ventricular LP to pace at an inappropriate high-rate, and more generally, at inappropriate times.

Such messages may include redundant data for error detection and correction. However, due to the desire to keep the power consumption low, the messaging and/or error correction and detection scheme may be simple and false messages may still get through.

SUMMARY

Implantable medical devices (IMDs), and methods for use therewith, reduce how often an IMD accepts false messages. Such a method can include receiving a message and performing error detection and correction on the message. Such a method can also include determining a quality measure indicative of at least one of a quality of the message or a quality of a channel over which the message was received, and determining whether to reject the message based on the quality measure.

Where the quality measure is indicative of a quality of the message, the quality of the message can be based on results of the error detection and correction. More specifically, the results of the error detection and correction can specify one of at least two different levels of message quality. In such embodiments, a method can include mapping the results of the error detection and correction to one of at least two different numbers, adjusting an average message quality based on the number, and comparing the average message quality to one or more thresholds. The method can further include determining whether to reject the message based on results of the comparing the average message quality to the one or more thresholds. The mapping the results of the error detection and correction to one number of at least two different numbers can include mapping the results of the error detection and correction to a first number if the results indicated the message was cleanly received without any correcting being needed, mapping the results of the error detection and correction to a second number that is less than the first number if the results indicated the message was corrected, and mapping the results of the error detection and correction to a third number that is less than the second number if the results indicated the message was uncorrectable. In such an embodiment, the average message quality can be adjusted using an equation $Q=(1-1/b)*Q+N*(1/b)$, where Q is the average message quality, N is the number to which the results of the error detection and correction was mapped, and b is a time constant parameter that controls a rate of change.

In accordance with certain embodiments, the quality measure is based on whether an amplitude or power of a received signal including the message is within an expected amplitude or power range. Alternatively, or additionally, the quality measure can be based on whether a timing of the message is within an expected timing range.

In accordance with certain embodiments, the determining whether to reject the message includes determining that the message should be rejected if the quality measure is below a corresponding lower threshold, determining that the message should not be rejected if the quality measure is above a corresponding upper threshold, and if the quality measure is between the corresponding lower and upper thresholds, then determining that the message should be rejected if the preceding message was rejected, and determining that the message should not be rejected if the preceding message was not rejected.

In accordance with certain embodiments, where the quality measure is indicative of the quality of the channel over which the message was received, a method can include measuring noise associated with the channel over which the message was received, and determining the quality of the channel over which the message was received based on the measured noise associated with the channel.

In accordance with certain embodiments, an IMD includes at least one receiver configured to receive messages, and a processor and/or controller. The processor and/or controller can be configured to perform error detection and correction on a message received by the at least one receiver, determine a quality measure indicative of at least one of a quality of the message or a quality of a channel over which the message was received, and determine whether to reject the message based on the quality measure.

In accordance with certain embodiments, the IMD is a leadless pacemaker (LP) configured to be implanted in a ventricle of a patient's heart and configured to selectively deliver ventricular pacing pules. The messages can be received from another LP that is configured to be implanted in an atrium of a patient's heart and configured to at least one of sense intrinsic atrial depolarizations or selectively deliver atrial pacing pulses. The messages can be indicative of when the other LP sensed an intrinsic atrial depolarization or delivered an atrial pacing pulse. Such a message, if accepted, can be used to trigger an atrioventricular interval (AVI) timer of the LP.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

BRIEF DESCRIPTION OF THE DRAWINGS

Embodiments of the present technology relating to both structure and method of operation may best be understood by referring to the following description and accompanying drawings, in which similar reference characters denote similar elements throughout the several views.

DETAILED DESCRIPTION

Certain embodiments of the present technology related to implantable medical devices (IMDs), and methods for use therewith, that reduce how often false messages are accepted. Such a method can include receiving a message and measuring a message interval indicative of a length of time between when the message was received and when a preceding message was received. The method can also include determining, based on the measured message interval, whether the message was received within the message window, and determining whether to reject the message based on results thereof. The method can also include adjusting a temporal position of the message window based on the measured message interval. A method can additionally or alternatively include determining a quality measure indicative of a quality of the message and/or a quality of a channel over which the message was received, and determining whether to reject the message based on the quality measure.

Before providing addition details of the specific embodiments of the present technology mentioned above, an exemplary system in which embodiments of the present technology can be used with first be described with reference to FIGS. 1-5. More specifically, FIGS. 1-5 will be used to describe an exemplary cardiac pacing system, wherein pacing and sensing operations can be performed by multiple medical devices, which may include one or more leadless cardiac pacemakers, an ICD, such as a subcutaneous-ICD, and/or a programmer reliably and safely coordinate pacing and/or sensing operations.

Figure 1:
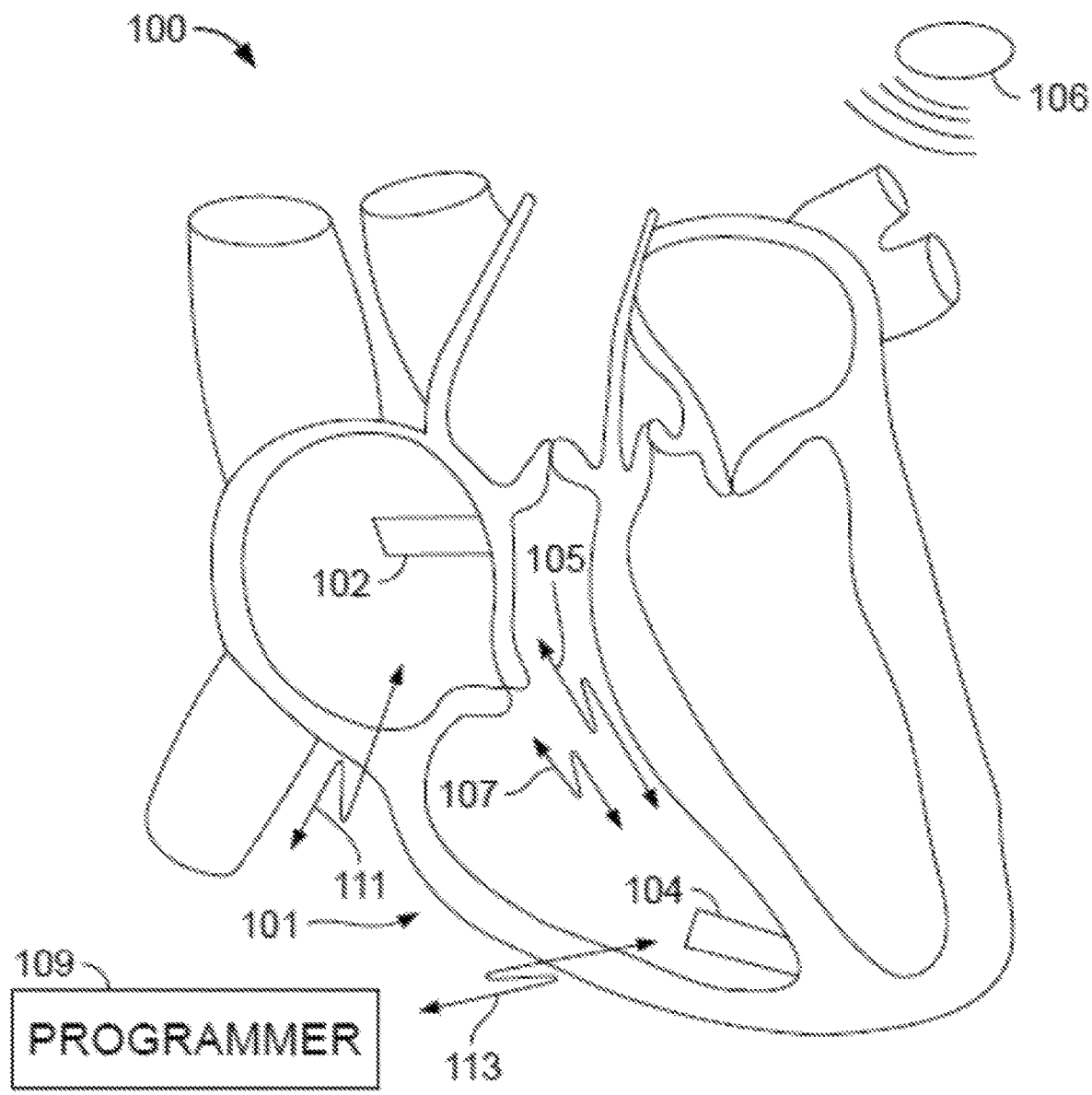
FIG. 1 illustrates a system formed in accordance with certain embodiments herein as implanted in a heart.

FIG. 1 illustrates a system 100 that is configured to be implanted in a heart 101. The system 100 comprises two or more leadless pacemakers (LPs) 102 and 104 located in different chambers of the heart. LP 102 is located in a right atrium, while LP 104 is located in a right ventricle. LPs 102 and 104 communicate with one another to inform one another of various local physiologic activities, such as local intrinsic events, local paced events and the like. LPs 102 and 104 may be constructed in a similar manner, but operate differently based upon which chamber LP 102 or 104 is located.

In some embodiments, LPs 102 and 104 communicate with one another, with an ICD 106, and with an external device (programmer) 109 through wireless transceivers, communication coils and antenna, and/or by conductive communication through the same electrodes as used for sensing and/or delivery of pacing therapy. When conductive communication is maintained through the same electrodes as used for pacing, the system 100 may omit an antenna or telemetry coil in one or more of LPs 102 and 104.

In some embodiments, one or more leadless cardiac pacemakers 102 and 104 can be co-implanted with the implantable cardioverter-defibrillator (ICD) 106. Each leadless cardiac pacemaker 102, 104 uses two or more electrodes located within, on, or within a few centimeters of the housing of the pacemaker, for pacing and sensing at the cardiac chamber, for bidirectional communication with one another, with the programmer 109, and the ICD 106.

In accordance with certain embodiments, methods are provided for coordinating operation between leadless pacemakers (LPs) located in different chambers of the heart. The methods configure a local LP to receive communications from a remote LP through conductive communication.

While the methods and systems described herein include examples primarily in the context of LPs, it is understood that the methods and systems herein may be utilized with various other external and implanted devices. By way of example, the methods and systems may coordinate operation between various implantable medical devices (IMDs) implanted in a human, not just LPs. The methods and systems comprise configuring a first IMD to receive communications from at least a second IMD through conductive communication over at least a first channel. It should also be understood that the methods and systems may coordinate operation between multiple IMDs, and are not limited to coordinate operation between just a first and second IMD. The methods and systems may also be used to coordinate operation of two or more IMDs implanted within the same chamber that may be the same type of IMD or may be different types of IMDs. The methods and systems may also be used to coordinate operation of two or more IMDs in a system comprising at least one IMD implanted but not within a heart chamber, e.g., epicardially, transmurally, intravascularly (e.g., coronary sinus), subcutaneously (e.g., S-ICD), etc.

Figure 2:
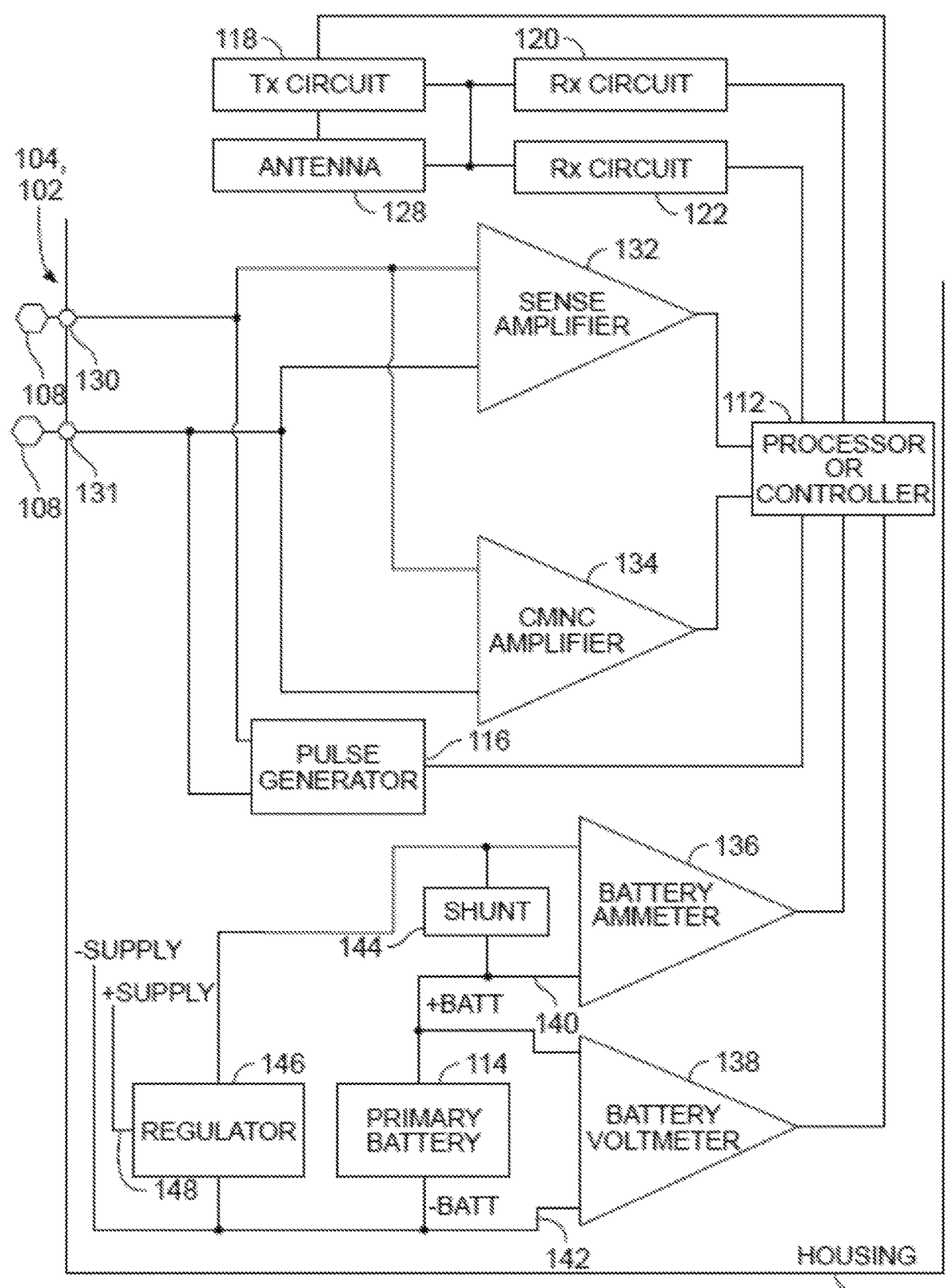
FIG. 2 is a block diagram of a single LP in accordance with certain embodiments herein.

Referring to FIG. 2, a pictorial diagram shows an embodiment for portions of the electronics within LP 102, 104 configured to provide conducted communication through the sensing/pacing electrode. One or more of LPs 102 and 104 comprise at least two leadless electrodes 108 configured for delivering cardiac pacing pulses, sensing evoked and/or natural cardiac electrical signals, and uni-directional or bi-directional communication.

LP 102, 104 includes a transmitter 118 and first and second receivers 120 and 122 that collectively define separate first and second communication channels 105 and 107 (FIG. 1), (among other things) between LPs 102 and 104. Although first and second receivers 120 and 122 are depicted, in other embodiments, LP 102, 104 may only include first receiver 120, or may include additional receivers other than first and second receivers 120 and 122. LP 102, 104 may only also include one or more transmitters in addition to transmitter 118. In certain embodiments, LPs 102 and 104 may communicate over more than just first and second communication channels 105 and 107. In certain embodiments, LPs 102 and 104 may communicate over one common communication channel 105. The transmitter 118 and receiver(s) 120, 122 may each utilize a separate antenna or may utilize a common antenna 128. Optionally, LPs 102 and 104 communicate conductively over a common physical channel via the same electrodes 108 that are also used to deliver pacing pulses. Usage of the electrodes 108 for communication enables the one or more leadless cardiac pacemakers 102 and 104 for antenna-less and telemetry coil-less communication.

When LP 102, 104 senses an intrinsic event or delivers a paced event, the corresponding LP 102, 104 transmits an implant event message to the other LP 102, 104. For example, when an atrial LP 102 senses/paces an atrial event, the atrial LP 102 transmits an implant event message including an event marker indicative of a nature of the event (e.g., intrinsic/sensed atrial event, paced atrial event). When a ventricular LP 104 senses/paces a ventricular event, the ventricular LP 104 transmits an implant event message including an event marker indicative of a nature of the event (e.g., intrinsic/sensed ventricular event, paced ventricular event). In certain embodiments, LP 102, 104 transmits an implant event message to the other LP 102, 104 preceding the actual pace pulse so that the remote LP can blank its sense inputs in anticipation of that remote pace pulse (to prevent inappropriate crosstalk sensing).

The implant event messages may be formatted in various manners. As one example, each event message may include a leading trigger pulse (also referred to as an LP wakeup notice or wakeup pulse) followed by an event marker. The notice trigger pulse is transmitted over a first channel (e.g., with a pulse duration of approximately 10 µs to approximately 1 ms and/or within a fundamental frequency range of approximately 1 kHz to approximately 100 kHz). The notice trigger pulse indicates that an event marker is about to be transmitted over a second channel (e.g., within a higher frequency range). The event marker can then be transmitted over the second channel.

The event markers may include data indicative of one or more events (e.g., a sensed intrinsic atrial activation for an atrial located LP, a sensed intrinsic ventricular activation for a ventricular located LP). The event markers may include different markers for intrinsic and paced events. The event markers may also indicate start or end times for timers (e.g., an AV interval, a blanking interval, etc.). Optionally, the implant event message may include a message segment that includes additional/secondary information.

Optionally, the LP (or other IMD) that receives any implant to implant (i2i) communication from another LP (or other IMD) or from an external device may transmit a receive acknowledgement indicating that the receiving LP/IMD received the i2i communication, etc.

The event messages enable the LPs 102, 104 to deliver synchronized therapy and additional supportive features (e.g., measurements, etc.). To maintain synchronous therapy, each of the LPs 102 and 104 is made aware (through the event messages) when an event occurs in the chamber containing the other LP 102, 104. Some embodiments described herein provide efficient and reliable processes to maintain synchronization between LPs 102 and 104 without maintaining continuous communication between LPs 102 and 104. In accordance with certain embodiments herein, the transmitter(s) 118 and receiver(s) 120, 122 utilize low power event messages/signaling between multiple LPs 102 and 104. The low power event messages/signaling may be maintained between LPs 102 and 104 synchronously or asynchronously.

For synchronous event signaling, LPs 102 and 104 maintain synchronization and regularly communicate at a specific interval. Synchronous event signaling allows the transmitter and receivers in each LP 102, 104 to use limited (or minimal) power as each LP 102, 104 is only powered for a small fraction of the time in connection with transmission and reception. For example, LP 102, 104 may transmit/receive (Tx/Rx) communications in time slots having duration of 10-20 µs, where the Tx/Rx time slots occur periodically (e.g., every 10-20 ms). In the foregoing example, a receiver 120, 122 that is active/ON (also referred to as awake) for select receive time slots, that are spaced apart several milliseconds, may draw an amount of current that is several times less (e.g., 1000× less) than a current draw of a receiver that is "always on" (always awake).

LPs 102 and 104 may lose synchronization, even in a synchronous event signaling scheme. As explained herein, features may be included in LPs 102 and 104 to maintain device synchronization, and when synchronization is lost, LPs 102 and 104 undergo operations to recover synchronization. Also, synchronous event messages/signaling may introduce a delay between transmissions which causes a reaction lag at the receiving LP 102, 104. Accordingly, features may be implemented to account for the reaction lag.

During asynchronous event signaling, LPs 102 and 104 do not maintain communication synchronization. During asynchronous event signaling, one or more of receivers 120 and 122 of LPs 102 and 104 may be "always on" (always awake) to search for incoming transmissions. However, maintaining LP receivers 120, 122 in an "always on" (always awake) state presents challenges as the received signal level often is low due to high channel attenuation caused by the patient's anatomy. Further, maintaining the receivers awake will deplete the battery 114 more quickly than may be desirable.

The asynchronous event signaling methods avoid risks associated with losing synchronization between devices. However, the asynchronous event signaling methods utilize additional receiver current between transmissions. For purposes of illustration only, a non-limiting example is described hereafter. For example, the channel attenuation may be estimated to have a gain of $\frac{1}{500}$ to $\frac{1}{10000}$. A gain factor may be $\frac{1}{1000}$th. Transmit current is a design factor in addition to receiver current. As an example, the system may allocate one-half of the implant communication current budget to the transmitter (e.g., 0.5 µA for each transmitter). When LP 102, 104 maintains a transmitter in a continuous on-state and the electrode load is 500 ohms, a transmitted voltage may be 0.250 mV. When an event signal is transmitted at 0.250 mV, the event signal is attenuated as it propagates and would appear at LP 102, 104 receiver as an amplitude of approximately 0.25 µV. The receivers 120 and 122 can utilize a synchronization threshold to help differentiate incoming communication signals from noise. As an example, the synchronization threshold may be 0.5 µV (or more generally 0.25 µV to 5 µV), which would cause LP 102, 104 receiver to reject an incoming communication signal that exhibits a receive voltage below 0.5 µV. Nevertheless, even with the use of the synchronization threshold, noise may still be mistaken as being communication signals, and more specifically, as being messages.

To overcome the foregoing receive power limit, a pulsed transmission scheme may be utilized in which communication transmissions occur correlated with an event. By way of example, the pulsed transmission scheme may be simplified such that each transmission constitutes a single pulse of a select amplitude and width.

When LP transmitter 118 transmits event signals over a conductive communication channel that has an electrode load of 500 ohm using a 1 ms pulse width at 2.5V at a rate of 60 bpm, LP transmitter 118 will draw 4.4 µA for transmit current. When LP transmitter 118 transmits event signals at 2.5V using a 2 µs pulse width, transmitter 118 only draws 10 µA to transmit event messages at a rate of 60 bpm. In order to sense an event message (transmitted with the foregoing parameters), receivers 120 and 122 may utilize 50 µA. In accordance with certain embodiments herein, the pulse widths and other transmit/receive parameters may be adjusted to achieve a desired total (summed) current demand from both transmitter 118 and receivers 120 and 122. The transmitter current decreases nearly linearly with narrowing bandwidth (pulse width), while a relation between receiver current and bandwidth is non-linear.

In accordance with certain embodiments herein, LPs 102 and 104 may utilize multi-stage receivers that implement a staged receiver wakeup scheme in order to improve reliability yet remain power efficient. Each of LPs 102 and 104 may include first and second receivers 120 and 122 that operate with different first and second activation protocols and different first and second receive channels. For example, first receiver 120 may be assigned a first activation protocol that is "always on" (also referred to as always awake) and that listens over a first receive channel that has a lower fundamental frequency range/pulse duration (e.g., 1 kHz to 100 kHz/10 µs to approximately 1 ms) as compared to the fundamental frequency range (e.g., greater than 100 kHz/less than 10 µs per pulse) assigned to the second receive channel. First receiver 120 may maintain the first channel active (awake) for at least a portion of a time when the second channel is inactive (asleep) to listen for event messages from a remote LP. The controller or processor determines whether the incoming signal received over the first channel corresponds to an LP wakeup notice. The second receiver 122 may be assigned a second activation protocol that is a triggered protocol, in which the second receiver 122 becomes active (awake) in response to detection of trigger events over the first receive channel (e.g., when the incoming signal corresponds to the LP wakeup notice, activating the second channel at the local LP).

The marker message may represent a signature indicative of an event qualification to qualify a valid event marker pulse. The event qualification messages distinguish a message from spurious noise and avoid mistaking other signals as event messages having implant markers. The event message may be repeated to allow the LP receiver 120 multiple chances to "catch" the event qualification. Additionally or alternatively, the Tx and Rx LP 102, 104 may implement a handshaking protocol in which the Tx and Rx LP 102, 104 exchange additional information, such as to allow a response to follow the marker. The exchange of additional information may be limited or avoided in certain instances as the exchange draws additional power when sending and receiving the information. Optionally, the event message may be configured with additional content to provide a more robust event marker.

Transmitter 118 may be configured to transmit the event messages in a manner that does not inadvertently capture the heart in the chamber where LP 102, 104 is located, such as when the associated chamber is not in a refractory state. In addition, a LP 102, 104 that receives an event message may enter an "event refractory" state (or event blanking state) following receipt of the event message. The event refractory/blanking state may be set to extend for a determined period of time after receipt of an event message in order to avoid the receiving LP 102, 104 from inadvertently sensing another signal as an event message that might otherwise cause retriggering. For example, the receiving LP 102, 104 may detect a measurement pulse from another LP 102, 104 or programmer 109.

In accordance with certain embodiments herein, programmer 109 may communicate over a programmer-to-LP channel, with LP 102, 104 utilizing the same communication scheme. The external programmer may listen to the event message transmitted between LP 102, 104 and synchronize programmer to implant communication such that programmer 109 does not transmit communication signals 113 until after an implant to implant messaging sequence is completed.

In accordance with certain embodiments, LP 102, 104 may combine transmit operations with therapy. The transmit event marker may be configured to have similar characteristics in amplitude and pulse width to a pacing pulse and LP 102, 104 may use the energy in the event messages to help capture the heart. For example, a pacing pulse may normally be delivered with pacing parameters of 2.5V amplitude, 500 ohm impedance, 60 bpm pacing rate, 0.4 ms pulse width. The foregoing pacing parameters correspond to a current draw of about 1.9 µA. The same LP 102, 104 may implement an event message utilizing event signaling parameters for amplitude, pulse width, pulse rate, etc. that correspond to a current draw of approximately 0.5 µA for transmit.

LP 102, 104 may combine the event message transmissions with pacing pulses. For example, LP 102, 104 may use a 50 µs wakeup transmit pulse having an amplitude of 2.5V which would draw 250 nC (nano Coulombs) for an electrode load of 500 ohm. The pulses of the transmit event message may be followed by an event message encoded with a sequence of short duration pulses (for example 16, 2 µs on/off bits) which would draw an additional 80 nC. The event message pulse would then be followed by the remaining pulse width needed to reach an equivalent charge of a nominal 0.4 ms pace pulse. In this case, the current necessary to transmit the marker is essentially free as it was used to achieve the necessary pace capture anyhow. With this method, the savings in transmit current could be budgeted for the receiver or would allow for additional longevity.

When LP 102, 104 senses an intrinsic event, the transmitter sends a qualitatively similar event pulse sequence (but indicative of a sensed event) without adding the pace pulse remainder. As LP 102, 104 longevity calculations are designed based on the assumption that LP 102, 104 will deliver pacing therapy 100% of the time, transmitting an intrinsic event marker to another LP 102, 104 will not impact the nominal calculated LP longevity.

In some embodiments, LP 102, 104 may deliver pacing pulses at relatively low amplitude. When low amplitude pacing pulses are used, the power budget for event messages may be modified to be a larger portion of the overall device energy budget. As the pacing pulse amplitude is lowered closer to amplitude of event messages, LP 102, 104 increases an extent to which LP 102, 104 uses the event messages as part of the pacing therapy (also referred to as sharing "capture charge" and "transmit charge"). As an example, if the nominal pacing voltage can be lowered to <1.25 V, then a "supply halving" pacing charge circuit could reduce the battery current draw by approximately 50%. A 1.25V pace pulse would save 1.5 µA of pacing current budget. With lower pulse amplitudes, LP 102, 104 may use larger pulse widths.

By combining event messages and low power pacing, LP 102, 104 may realize additional longevity. Today longevity standards provide that the longevity to be specified based on a therapy that utilizes 2.5V amplitude, 0.4 ms pulses at 100% pacing. Optionally, a new standard may be established based on pacing pulses that deliver lower amplitude and/or shorter pacing pulses.

In an embodiment, a communication capacitor is provided in LP 102, 104. The communication capacitor may be used to transmit event signals having higher voltage for the event message pulses to improve communication, such as when the LPs 102 and 104 experience difficulty sensing event messages. The high voltage event signaling may be used for implants with high signal attenuation or in the case of a retry for an ARQ (automatic repeat request) handshaking scheme.

For example, when an LP 102, 104 does not receive an event message within a select time out interval, LP 102, 104 may resend an event message at a higher amplitude. As another example, LP 102, 104 may perform an event signaling auto-level search wherein the LPs send event messages at progressively higher amplitude until receiving confirmation that an event message was received (or receiving a subsequent event message from another LP). For example, in DDD mode when the atrial or ventricular LP 102, 104 does not see an event signal from LP 102, 104 in the other chamber before its timeout interval it could automatically raise the amplitude of the event message, until the LPs 102 and 104 become and remain in sync. Optionally, LP 102, 104 may implement a search hysteresis algorithm similar to those used for rate and amplitude capture to allow the lowest safe detectible amplitude to be determined.

The LPs 102 and 104 may be programmable such as to afford flexibility in adjusting the event marker pulse width. In some embodiments, different receiver circuits may be provided and selected for certain pulse widths, where multiple receivers may be provided on a common ASIC, thereby allowing the user to vary the parameters in an LP after implant.

In some embodiments, the individual LP 102 can comprise a hermetic housing 110 configured for placement on or attachment to the inside or outside of a cardiac chamber and at least two leadless electrodes 108 proximal to the housing 110 and configured for bidirectional communication with at least one other device 106 within or outside the body.

FIG. 2 depicts a single LP 102 and shows the LP's functional elements substantially enclosed in a hermetic housing 110. The LP 102 has at least two electrodes 108 located within, on, or near the housing 110, for delivering pacing pulses to and sensing electrical activity from the muscle of the cardiac chamber, and for bidirectional communication with at least one other device within or outside the body. Hermetic feedthroughs 130, 131 conduct electrode signals through the housing 110. The housing 110 contains a primary battery 114 to supply power for pacing, sensing, and communication. The housing 110 also contains circuits 132 for sensing cardiac activity from the electrodes 108, circuits 134 for receiving information from at least one other device via the electrodes 108, and a pulse generator 116 for generating pacing pulses for delivery via the electrodes 108 and also for transmitting information to at least one other device via the electrodes 108. The housing 110 can further contain circuits for monitoring device health, for example a battery current monitor 136 and a battery voltage monitor 138, and can contain circuits for controlling operations in a predetermined manner.

Additionally or alternatively, one or more leadless electrodes 108 can be configured to communicate bidirectionally among the multiple leadless cardiac pacemakers and/or the implanted ICD 106 to coordinate pacing pulse delivery and optionally other therapeutic or diagnostic features using messages that identify an event at an individual pacemaker originating the message and a pacemaker receiving the message react as directed by the message depending on the origin of the message. An LP 102, 104 that receives the event message reacts as directed by the event message depending on the message origin or location. In some embodiments or conditions, the two or more leadless electrodes 108 can be configured to communicate bidirectionally among the one or more leadless cardiac pacemakers 102 and/or the ICD 106 and transmit data including designated codes for events detected or created by an individual pacemaker. Individual pacemakers can be configured to issue a unique code corresponding to an event type and a location of the sending pacemaker.

In some embodiments, an individual LP 102, 104 can be configured to deliver a pacing pulse with an event message encoded therein, with a code assigned according to pacemaker location and configured to transmit a message to one or more other leadless cardiac pacemakers via the event message coded pacing pulse. The pacemaker or pacemakers receiving the message are adapted to respond to the message in a predetermined manner depending on type and location of the event.

Moreover, information communicated on the incoming channel can also include an event message from another leadless cardiac pacemaker signifying that the other leadless cardiac pacemaker has sensed a heartbeat or has delivered a pacing pulse, and identifies the location of the other pacemaker. For example, LP 104 may receive and relay an event message from LP 102 to the programmer. Similarly, information communicated on the outgoing channel can also include a message to another leadless cardiac pacemaker or pacemakers, or to the ICD, that the sending leadless cardiac pacemaker has sensed a heartbeat or has delivered a pacing pulse at the location of the sending pacemaker.

Referring again to FIGS. 1 and 2, the cardiac pacing system 100 may comprise an implantable cardioverter-defibrillator (ICD) 106 in addition to leadless cardiac pacemaker 102, 104 configured for implantation in electrical contact with a cardiac chamber and for performing cardiac rhythm management functions in combination with the implantable ICD 106. The implantable ICD 106 and the one or more leadless cardiac pacemakers 102, 104 configured for leadless intercommunication by information conduction through body tissue and/or wireless transmission between transmitters and receivers in accordance with the discussed herein.

In a further embodiment, a cardiac pacing system 100 comprises at least one leadless cardiac pacemaker 102, 104 configured for implantation in electrical contact with a cardiac chamber and configured to perform cardiac pacing functions in combination with the co-implanted implantable cardioverter-defibrillator (ICD) 106. The leadless cardiac pacemaker or pacemakers 102 comprise at least two leadless electrodes 108 configured for delivering cardiac pacing pulses, sensing evoked and/or natural cardiac electrical signals, and transmitting information to the co-implanted ICD 106.

As shown in the illustrative embodiments, a leadless cardiac pacemaker 102, 104 can comprise two or more leadless electrodes 108 configured for delivering cardiac pacing pulses, sensing evoked and/or natural cardiac electrical signals, and bidirectionally communicating with the co-implanted ICD 106.

LP 102, 104 can be configured for operation in a particular location and a particular functionality at manufacture and/or at programming by an external programmer. Bidirectional communication among the multiple leadless cardiac pacemakers can be arranged to communicate notification of a sensed heartbeat or delivered pacing pulse event and encoding type and location of the event to another implanted pacemaker or pacemakers. LP 102, 104 receiving the communication decode the information and respond depending on location of the receiving pacemaker and predetermined system functionality.

Also shown in FIG. 2, the primary battery 114 has positive terminal 140 and negative terminal 142. Current from the positive terminal 140 of primary battery 114 flows through a shunt 144 to a regulator circuit 146 to create a positive voltage supply 148 suitable for powering the remaining circuitry of the pacemaker 102. The shunt 144 enables the battery current monitor 136 to provide the processor 112 with an indication of battery current drain and indirectly of device health. The illustrative power supply can be a primary battery 114.

In various embodiments, LP 102, 104 can manage power consumption to draw limited power from the battery, thereby reducing device volume. Each circuit in the system can be designed to avoid large peak currents. For example, cardiac pacing can be achieved by discharging a tank capacitor (not shown) across the pacing electrodes. Recharging of the tank capacitor is typically controlled by a charge pump circuit. In a particular embodiment, the charge pump circuit is throttled to recharge the tank capacitor at constant power from the battery.

In some embodiments, the controller 112 in one leadless cardiac pacemaker 102 can access signals on the electrodes 108 and can examine output pulse duration from another pacemaker for usage as a signature for determining triggering information validity and, for a signature arriving within predetermined limits, activating delivery of a pacing pulse following a predetermined delay of zero or more milliseconds. The predetermined delay can be preset at manufacture, programmed via an external programmer, or determined by adaptive monitoring to facilitate recognition of the triggering signal and discriminating the triggering signal from noise. In some embodiments or in some conditions, the controller 112 can examine output pulse waveform from another leadless cardiac pacemaker for usage as a signature for determining triggering information validity and, for a signature arriving within predetermined limits, activating delivery of a pacing pulse following a predetermined delay of zero or more milliseconds.

Figure 3:
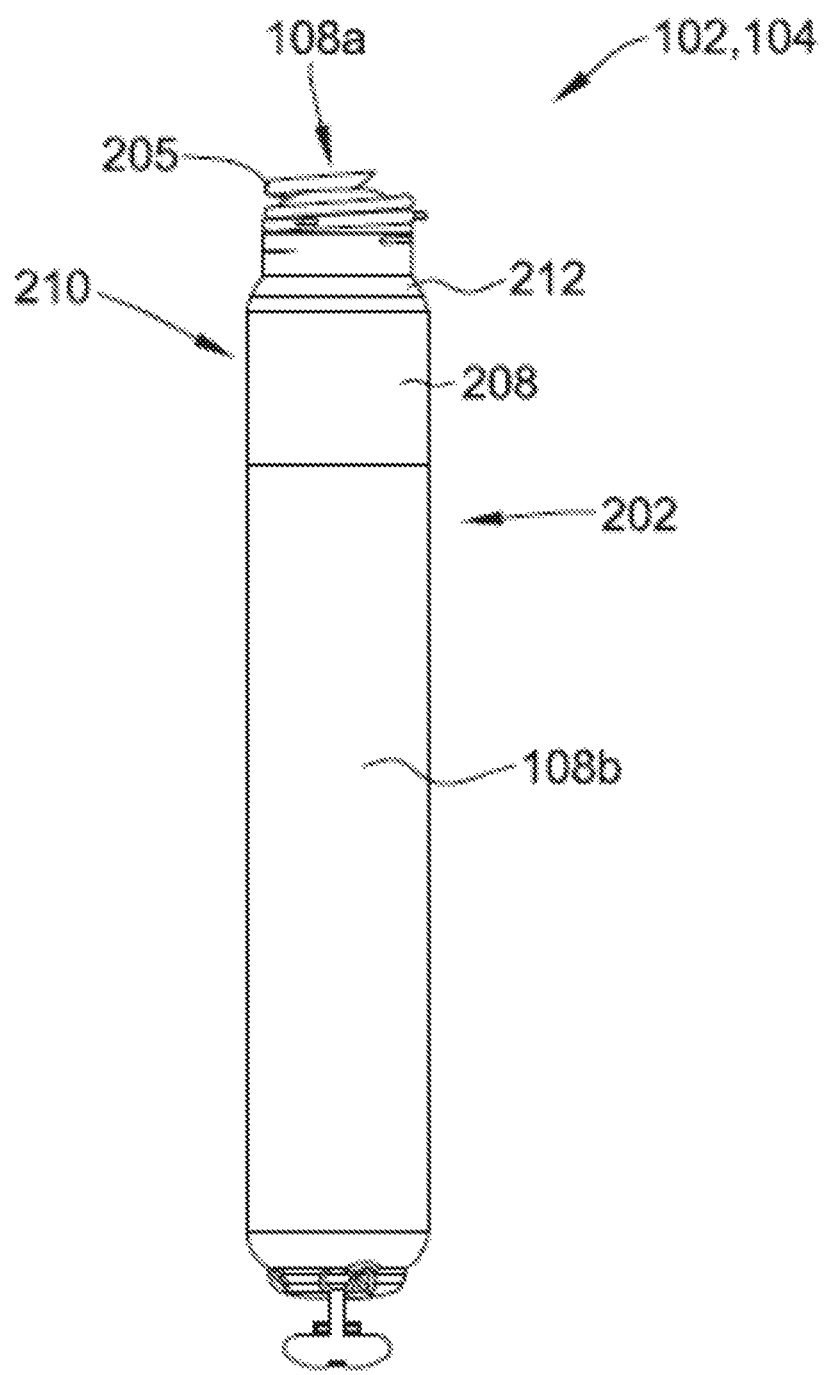
FIG. 3 illustrates an LP in accordance with certain embodiments herein.

FIG. 3 shows an LP 102, 104. The LP can include a hermetic housing 202 with electrodes 108a and 108b disposed thereon. As shown, electrode 108a can be separated from but surrounded partially by a fixation mechanism 205, and the electrode 108b can be disposed on the housing 202. The fixation mechanism 205 can be a fixation helix, a plurality of hooks, barbs, or other attaching features configured to attach the pacemaker to tissue, such as heart tissue.

The housing can also include an electronics compartment 210 within the housing that contains the electronic components necessary for operation of the pacemaker, including, for example, a pulse generator, communication electronics, a battery, and a processor for operation. The hermetic housing 202 can be adapted to be implanted on or in a human heart, and can be cylindrically shaped, rectangular, spherical, or any other appropriate shapes, for example.

The housing can comprise a conductive, biocompatible, inert, and anodically safe material such as titanium, 316L stainless steel, or other similar materials. The housing can further comprise an insulator disposed on the conductive material to separate electrodes 108a and 108b. The insulator can be an insulative coating on a portion of the housing between the electrodes, and can comprise materials such as silicone, polyurethane, parylene, or another biocompatible electrical insulator commonly used for implantable medical devices. In the embodiment of FIG. 3, a single insulator 208 is disposed along the portion of the housing between electrodes 108a and 108b. In some embodiments, the housing itself can comprise an insulator instead of a conductor, such as an alumina ceramic or other similar materials, and the electrodes can be disposed upon the housing.

As shown in FIG. 3, the pacemaker can further include a header assembly 212 to isolate 108a and 108b. The header assembly 212 can be made from PEEK, tecothane or another biocompatible plastic, and can contain a ceramic to metal feedthrough, a glass to metal feedthrough, or other appropriate feedthrough insulator as known in the art.

The electrodes 108a and 108b can comprise pace/sense electrodes, or return electrodes. A low-polarization coating can be applied to the electrodes, such as sintered platinum, platinum-iridium, iridium, iridium-oxide, titanium-nitride, carbon, or other materials commonly used to reduce polarization effects, for example. In FIG. 3, electrode 108a can be a pace/sense electrode and electrode 108b can be a return electrode. The electrode 108b can be a portion of the conductive housing 202 that does not include an insulator 208.

Several techniques and structures can be used for attaching the housing 202 to the interior or exterior wall of the heart. A helical fixation mechanism 205, can enable insertion of the device endocardially or epicardially through a guiding catheter. A torqueable catheter can be used to rotate the housing and force the fixation device into heart tissue, thus affixing the fixation device (and also the electrode 108a in FIG. 3) into contact with stimulable tissue. Electrode 108b can serve as an indifferent electrode for sensing and pacing. The fixation mechanism may be coated partially or in full for electrical insulation, and a steroid-eluting matrix may be included on or near the device to minimize fibrotic reaction, as is known in conventional pacing electrode-leads.

Implant-to-Implant Event Messaging

LPs 102 and 104 can utilize implant-to-implant (i2i) communication through event messages to coordinate operation with one another in various manners. The terms i2i communication, i2i event messages, and i2i even markers are used interchangeably herein to refer to event related messages and IMD/IMD operation related messages transmitted from an implanted device and directed to another implanted device (although external devices, e.g., a programmer, may also receive i2i event messages). In certain embodiments, LP 102 and LP 104 operate as two independent leadless pacers maintaining beat-to-beat dual-chamber functionality via a "Master/Slave" operational configuration. For descriptive purposes, the ventricular LP 104 shall be referred to as "vLP" and the atrial LP 102 shall be referred to as "aLP". LP 102, 104 that is designated as the master device (e.g. vLP) may implement all or most dual-chamber diagnostic and therapy determination algorithms. For purposes of the following illustration, it is assumed that the vLP is a "master" device, while the aLP is a "slave" device. Alternatively, the aLP may be designated as the master device, while the vLP may be designated as the slave device. The master device orchestrates most or all decision-making and timing determinations (including, for example, rate-response changes).

In accordance with certain embodiments, methods are provided for coordinating operation between first and second leadless pacemakers (LPs) configured to be implanted entirely within first and second chambers of the heart. A method transmits an event marker through conductive communication through electrodes located along a housing of the first LP, the event marker indicative of one of a local paced or sensed event. The method detects, over a sensing channel, the event marker at the second LP. The method identifies the event marker at the second LP based on a predetermined pattern configured to indicate that an event of interest has occurred in a remote chamber. In response to the identifying operation, the method initiates a related action in the second LP.

Figure 4:
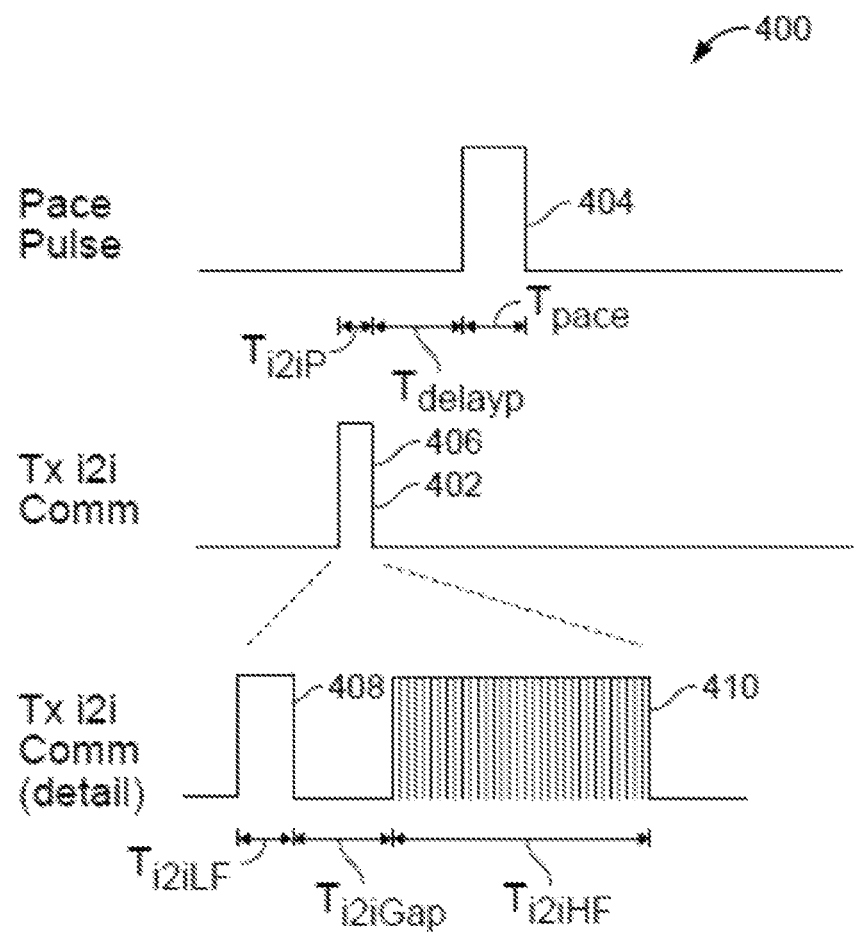
FIG. 4 is a timing diagram demonstrating one embodiment of implant to implant (i2i) communication for a paced event.

FIG. 4 is a timing diagram 400 demonstrating one example of an i2i communication for a paced event. The i2i communication may be transmitted, for example, from LP 102 to LP 104. As shown in FIG. 4, in this embodiment, an i2i transmission 402 is sent prior to delivery of a pace pulse 404 by the transmitting LP (e.g., LP 102). This enables the receiving LP (e.g., LP 104) to prepare for the remote delivery of the pace pulse. The i2i transmission 402 includes an envelope 406 that may include one or more individual pulses. For example, in this embodiment, envelope 406 includes a low frequency pulse 408 followed by a high frequency pulse train 410. Low frequency pulse 408 lasts for a period $T_{i2iLF}$, and high frequency pulse train 410 lasts for a period $T_{i2iHF}$. The end of low frequency pulse 408 and the beginning of high frequency pulse train 410 are separated by a gap period, $T_{i2iGap}$.

As shown in FIG. 4, the i2i transmission 402 lasts for a period Ti2iP, and pace pulse 404 lasts for a period Tpace. The end of i2i transmission 402 and the beginning of pace pulse 404 are separated by a delay period, TdelayP. The delay period may be, for example, between approximately 0.0 and 10.0 milliseconds (ms), particularly between approximately 0.1 ms and 2.0 ms, and more particularly approximately 1.0 ms. The term approximately, as used herein, means +/−10% of a specified value.

Figure 5:
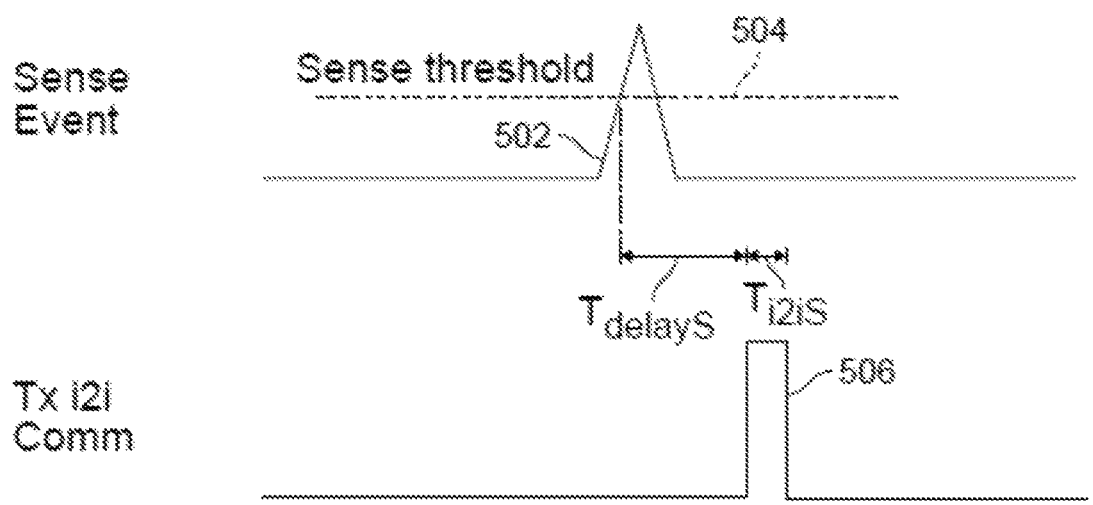
FIG. 5 is a timing diagram demonstrating one embodiment of i2i communication for a sensed event.

FIG. 5 is a timing diagram 500 demonstrating one example of an i2i communication for a sensed event. The i2i communication may be transmitted, for example, from LP 102 to LP 104. As shown in FIG. 5, in this embodiment, the transmitting LP (e.g., LP 102) detects the sensed event when a sensed intrinsic activation 502 crosses a sense threshold 504. A predetermined delay period, $T_{delayS}$, after the detection, the transmitting LP transmits an i2i transmission 506 that lasts a predetermined period $T_{i2iS}$. The delay period may be, for example, between approximately 0.0 and 10.0 milliseconds (ms), particularly between approximately 0.1 ms and 2.0 ms, and more particularly approximately 1.0 ms.

As with i2i transmission 402, i2i transmission 506 may include an envelope that may include one or more individual pulses. For example, similar to envelope 406, the envelope of i2i transmission 506 may include a low frequency pulse followed by a high frequency pulse train.

Optionally, wherein the first LP is located in an atrium and the second LP is located in a ventricle, the first LP produces an AS/AP event marker to indicate that an atrial sensed (AS) event or atrial paced (AP) event has occurred or will occur in the immediate future. For example, the AS and AP event markers may be transmitted following the corresponding AS or AP event. Alternatively, the first LP may transmit the AP event marker slightly prior to delivering an atrial pacing pulse. Alternatively, wherein the first LP is located in an atrium and the second LP is located in a ventricle, the second LP initiates an atrioventricular (AV) interval after receiving an AS or AP event marker from the first LP; and initiates a post atrial ventricular blanking (PAVB) interval after receiving an AP event marker from the first LP.

Optionally, the first and second LPs may operate in a "pure" master/slave relation, where the master LP delivers "command" markers in addition to or in place of "event" markers. A command marker directs the slave LP to perform an action such as to deliver a pacing pulse and the like. For example, when a slave LP is located in an atrium and a master LP is located in a ventricle, in a pure master/slave relation, the slave LP delivers an immediate pacing pulse to the atrium when receiving an AP command marker from the master LP.

In accordance with some embodiments, communication and synchronization between the aLP and vLP is implemented via conducted communication of markers/commands in the event messages (per i2i communication protocol). As explained above, conducted communication represents event messages transmitted from the sensing/pacing electrodes at frequencies outside the RF or Wi-Fi frequency range. Alternatively, the event messages may be conveyed over communication channels operating in the RF or Wi-Fi frequency range. The figures and corresponding description below illustrate non-limiting examples of markers that may be transmitted in event messages. The figures and corresponding description below also include the description of the markers and examples of results that occur in the LP that receives the event message. Table 1 represents exemplary event markers sent from the aLP to the vLP, while Table 2 represents exemplary event markers sent from the vLP to the aLP. In the master/slave configuration, AS event markers are sent from the aLP each time that an atrial event is sensed outside of the post ventricular atrial blanking (PVAB) interval or some other alternatively-defined atrial blanking period. The AP event markers are sent from the aLP each time that the aLP delivers a pacing pulse in the atrium. The aLP may restrict transmission of AS markers, whereby the aLP transmits AS event markers when atrial events are sensed both outside of the PVAB interval and outside the post ventricular atrial refractory period (PVARP) or some other alternatively-defined atrial refractory period. Alternatively, the aLP may not restrict transmission of AS event markers based on the PVARP, but instead transmit the AS event marker every time an atrial event is sensed.

TABLE 1

"A2V" Markers/Commands (i.e., from aLP to vLP)

| Marker | Description | Result in vLP |
|--------|-------------|---------------|
| AS | Notification of a sensed event in atrium (if not in PVAB or PVARP) | Initiate AV interval (if not in PVAB or PVARP) |
| AP | Notification of a paced event in atrium | Initiate PAVB Initiate AV interval (if not in PVARP) |

As shown in Table 1, when an aLP transmits an event message that includes an AS event marker (indicating that the aLP sensed an intrinsic atrial event), the vLP initiates an AV interval timer. If the aLP transmits an AS event marker for all sensed events, then the vLP would preferably first determine that a PVAB or PVARP interval is not active before initiating an AV interval timer. If however the aLP transmits an AS event marker only when an intrinsic signal is sensed outside of a PVAB or PVARP interval, then the vLP could initiate the AV interval timer upon receiving an AS event marker without first checking the PVAB or PVARP status. When the aLP transmits an AP event marker (indicating that the aLP delivered or is about to deliver a pace pulse to the atrium), the vLP initiates a PVAB timer and an AV interval time, provided that a PVARP interval is not active. The vLP may also blank its sense amplifiers to prevent possible crosstalk sensing of the remote pace pulse delivered by the aLP.

TABLE 2

"V2A" Markers/Commands (i.e., from vLP to aLP)

| Marker | Description | Result in aLP |
|---|---|---|
| VS | Notification of a sensed event in ventricle | Initiate PVARP |
| VP | Notification of a paced event in ventricle | Initiate PVAB<br>Initiate PVARP |
| AP | Command to deliver immediate pace pulse in atrium | Deliver immediate pace pulse to atrium |

As shown in Table 2, when the vLP senses a ventricular event, the vLP transmits an event message including a VS event marker, in response to which the aLP may initiate a PVARP interval timer. When the vLP delivers or is about to deliver a pace pulse in the ventricle, the vLP transmits VP event marker. When the aLP receives the VP event marker, the aLP initiates the PVAB interval timer and also the PVARP interval timer. The aLP may also blank its sense amplifiers to prevent possible crosstalk sensing of the remote pace pulse delivered by the vLP. The vLP may also transmit an event message containing an AP command marker to command the aLP to deliver an immediate pacing pulse in the atrium upon receipt of the command without delay.

The foregoing event markers are examples of a subset of markers that may be used to enable the aLP and vLP to maintain full dual chamber functionality. In one embodiment, the vLP may perform all dual-chamber algorithms, while the aLP may perform atrial-based hardware-related functions, such as PVAB, implemented locally within the aLP. In this embodiment, the aLP is effectively treated as a remote 'wireless' atrial pace/sense electrode. In another embodiment, the vLP may perform most but not all dual-chamber algorithms, while the aLP may perform a subset of diagnostic and therapeutic algorithms. In an alternative embodiment, vLP and aLP may equally perform diagnostic and therapeutic algorithms. In certain embodiments, decision responsibilities may be partitioned separately to one of the aLP or vLP. In other embodiments, decision responsibilities may involve joint inputs and responsibilities.

In an embodiment, ventricular-based pace and sense functionalities are not dependent on any i2i communication, in order to provide safer therapy. For example, in the event that LP to LP (i2i) communication is lost (prolonged or transient), the system 100 may automatically revert to safe ventricular-based pace/sense functionalities as the vLP device is running all of the necessary algorithms to independently achieve these functionalities. For example, the vLP may revert to a VVI mode as the vLP does not depend on i2i communication to perform ventricular pace/sense activities. Once i2i communication is restored, the system 100 can automatically resume dual-chamber functionalities.

Mitigating False Messages

As noted above, implantable medical devices and systems often rely on proper communications to operate correctly. For example, in a dual chamber pacemaker system, such as the one described above with reference to FIGS. 1-5, i2i communications are critical for proper synchronization of the system. However, noise may cause one or more devices of such a system to falsely detect a message and inappropriately respond thereto. For a more specific example, noise may cause a ventricular LP to falsely detect a message from an atrial LP, which then could trigger the ventricular LP to pace at an inappropriate high-rate, and more generally, at one or more inappropriate times. As also noted above, such messages can include redundant data for error detection and correction. However, due to the desire to keep the power consumption low, the messaging and/or error correction and detection scheme may be simple and false messages may still get through.

Certain embodiments of the present technology, which will be initially described with reference to the high level flow diagram of FIG. 6A, can be used to reduce how often an IMD, such as a ventricular LP (e.g., 104) or an atrial LP (e.g., 102), accept false messages. When a message is accepted by an IMD, the IMD may to trigger a timer, trigger an event and/or otherwise be responsive to the message to control or provide an instruction to the IMD that received the message. By contrast, when a message is rejected, this means that the message is prevented (e.g., blocked) from being used to trigger a timer, trigger an event and/or otherwise being used to control or provide an instruction to the IMD that received the message.

Figure 6A:
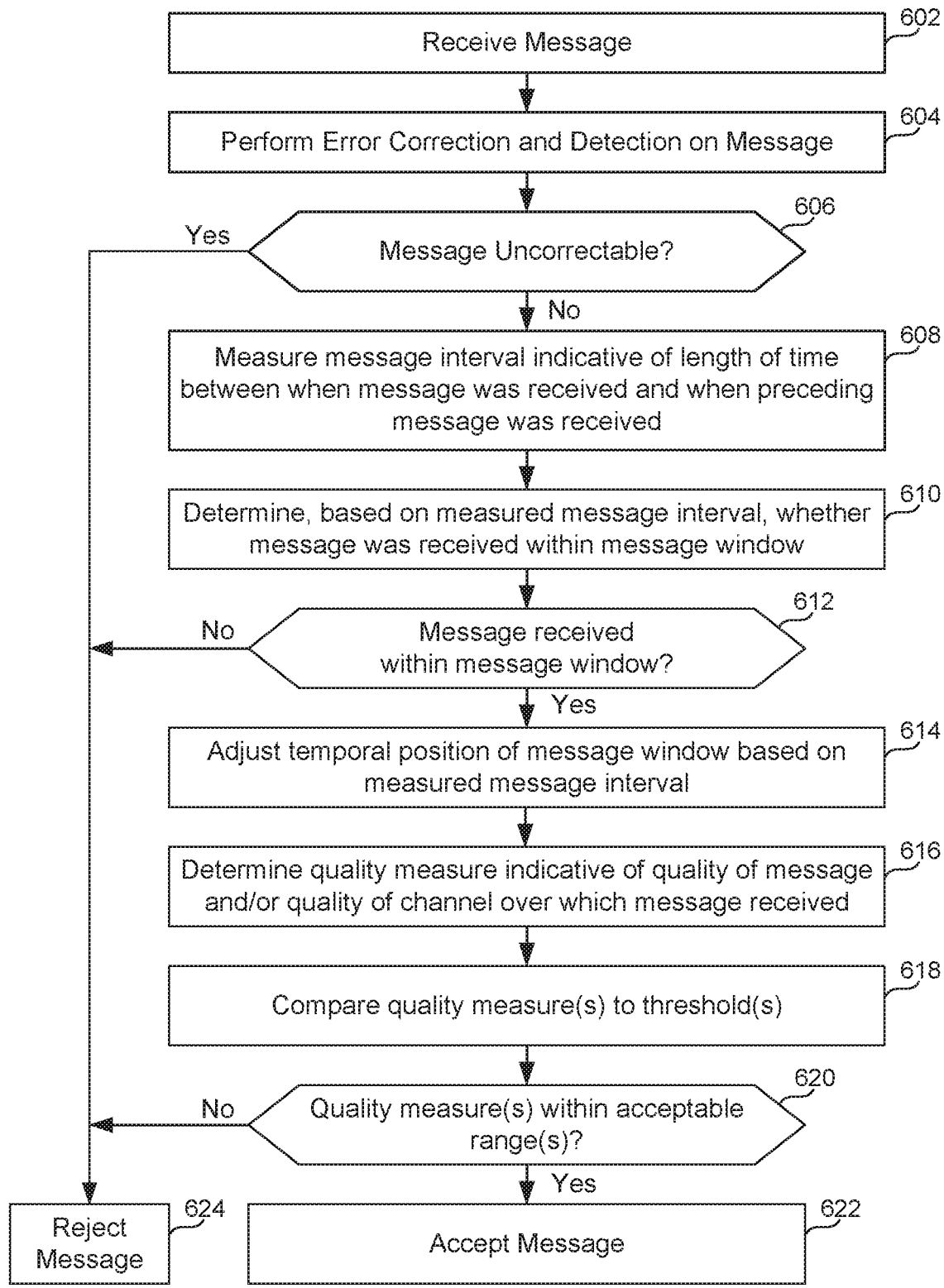
FIGS. 6A-6D are high level flow diagrams that are used to summarize methods according to certain embodiments of the present technology.

Referring to FIG. 6A, step 602 involves receiving a message, wherein the message that is received at step 602 may not actually be a true message, but rather, may be a false message. The term "message", as used herein, can refer to an actual sent message that is received and is capable of being decoded by an IMD, an actual sent message that is received but is too noisy to be decoded by the IMD, an actual sent message that is received but due to noise it is decoded mistakenly for a different message, noise that is received and is initially mistaken for being an actual message but cannot be decoded by the IMD because it is sufficiently different than an actual message, as well as noise that is received and is mistaken for being an actual message and is decoded by the IMD because it is sufficiently similar than an actual message. The term "false message", as used herein, refers to noise that is received and decoded by the IMD and is mistaken for being an actual message because it is sufficiently similar to an actual message. The term "false message", as used herein, can also refer to an actual sent message that is received but due to noise it is decoded mistakenly for a different message. The term "true message", as used herein, refers to an actual sent message that is received by an IMD and is correctly decoded by the IMD. An actual sent message may have been sent by another IMD, or alternatively, by a non-implanted device.

Still referring to FIG. 6A, step 604 involves performing error detection and correction on the message received at step 602. Error detection generally refers to the detection of errors caused by noise or other impairments during transmission from a transmitter of one device to a receiver of another device. Error correction generally refers to the detection of errors and reconstruction of the original, error-free data, if possible.

Typically, to enable error detection and correction to be performed, some redundancy (i.e., some extra data) is added to a message, which enables a receiver to check consistency of the received message, and to recover data determined to be corrupted. Error detection is often realized using a suitable hash function (or checksum algorithm) that adds a fixed-length tag to a message, which enables receivers to verify the delivered message by recomputing the tag and comparing it with the one provided. For example, a repetition code can be used, where a repetition code is a coding scheme that repeats the bits across a channel to attempt to achieve error-free communication. Such a repetition code is often inefficient, and can be susceptible to problems if the error occurs in exactly the same place for each group. However, an advantage of repetition codes is that they are extremely simple, and thus, are typically power efficient compared to more complex schemes. Instead of, or in addition to a repetition code, parity bits can be used, wherein a parity bit is a bit that is added to a group of source bits to ensure that a number of set bits (e.g., bits with value 1) in the outcome is even or odd. Alternatively, or additionally, checksums and/or cyclic redundancy checks can be utilized. A checksum of a message is a modular arithmetic sum of message code words of a fixed word length (e.g., byte values). The sum may be negated by means of a ones'-complement operation prior to transmission to detect errors resulting in all-zero messages. Checksum schemes can include parity bits, check digits, and longitudinal redundancy checks. A cyclic redundancy check (CRC) is a non-secure hash function designed to detect accidental changes to digital data.

Where an error is detected in a received message, such an error may often be corrected. Such error correction may involve the use of an automatic repeat request, an error-correcting code or a hybrid scheme, but is not limited thereto. Automatic repeat request (ARQ) is an error control technique for data transmission that makes use of error-detection codes, acknowledgment and/or negative acknowledgment messages, and timeouts to achieve reliable data transmission. An acknowledgment is a message sent by the receiver to indicate that it has correctly received a data frame. Usually, when a transmitter does not receive the acknowledgment before the timeout occurs (e.g., within a reasonable amount of time after sending the data frame), it retransmits the frame until it is either correctly received or the error persists beyond a predetermined number of retransmissions. An error-correcting code (ECC) or forward error correction (FEC) code is a process of adding redundant data, or parity data, to a message, such that it can be recovered by a receiver even when a number of errors (up to the capability of the code being used) were introduced, either during the process of transmission, or on storage. Since the receiver does not have to ask the sender for retransmission of the data, a backchannel is not required in forward error correction, and it is therefore suitable for simplex communication such as broadcasting. Hybrid ARQ is a combination of ARQ and forward error correction.

The above description has been included to provide a high level of possible error correction and detection schemes, and is not intended to be limiting and/or all encompassing, as the embodiments of the present technology can be used with almost any already developed or future developed error correction and detection schemes.

Still referring to FIG. 6A, at decision step 606, there is a determination of whether the received message was uncorrectable, i.e., was not corrected at step 604. If the answer to the determination at step 606 is YES, then the message is rejected, as indicated at step 624. As noted above, if the message is rejected, this means that the message is prevented (e.g., blocked) from being used to trigger a timer, trigger an event and/or otherwise being used to control or provide an instruction to the IMD that received the message. If the message was not uncorrectable, e.g., because it was received cleanly, or was corrected at step 604, then the answer to the determination at step 606 is NO and flow goes to step 608.

Figure 7:
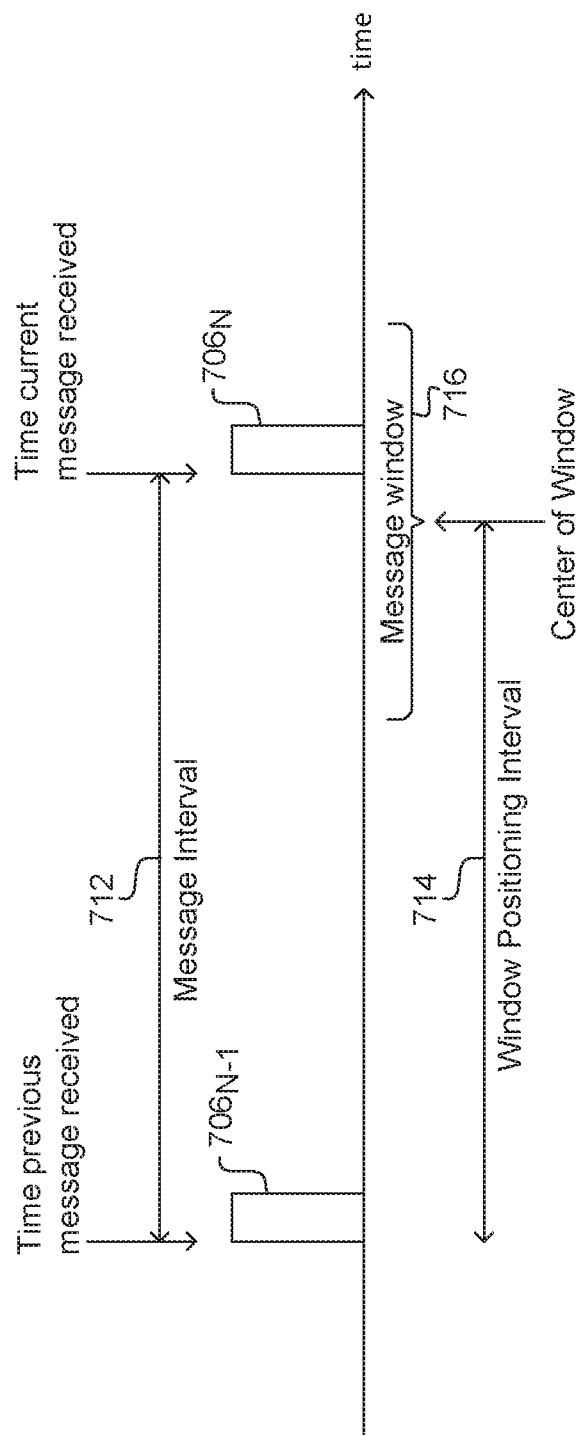
FIG. 7 is a timing diagram illustrating an exemplary message interval, an exemplary message window and an exemplary window positioning interval.

Step 608 involves measuring a message interval indicative of a length of time between when the message was received and when a preceding message was received. An example of such a message interval is shown in FIG. 7, which is a timing diagram illustrating an exemplary message interval 712, an exemplary message window 716 and an exemplary window positioning interval 714. Referring briefly to FIG. 7, the message that is received at step 602 is represented by the i2i transmission $706_N$, and the preceding message (that was received during a previous instance of step 602) is represented by the i2i transmission $706_{N-1}$. The message interval 712 that is measured at step 608 is the length of time between when the message (represented by the i2i transmission $706_N$) was received and when the preceding message (represented by the i2i transmission $706_{N-1}$) was received. As can be appreciated from FIG. 7, the window positioning interval 714 is indicative of a length of time between when the preceding message (represented by the i2i transmission $706_{N-1}$) was received and a center of a message window 716, wherein the message window 716 specifies a window or range of time during which it is expected that a message may be received. The width of the message window 716 may be fixed (e.g., 200 ms, but not limited thereto), or as will be described below, may be variable.

Referring again to FIG. 6A, step 610 involves determining, based on the measured message interval, whether the message was received within the message window. At decision step 612, there is a determination, based on the results of step 610, of whether the message was received within the message window. Referring briefly to FIG. 7, in this example, the message $706_N$ is shown as being received within the message window 716. Accordingly, the answer to the determination at step 612 would be YES. However, it can be appreciated from FIG. 7 that it is also possible that the message $706_N$ could have been received prior to or after the message window 716, in which case the answer to the determination at step 612 would be NO, and the message would be rejected at indicated step 624. More generally, certain embodiments of the present technology involve determining that a message should be rejected if the message was not received within a message window, and determining that the message should not be rejected if the message was received within the message window. This is because there is a high probability that a received message is a false message if the message is received outside the message window, and more specifically, outside of when the message is expected.

Referring again to FIG. 6A, if the answer to the determination at step 612 is YES, then flow goes to step 614, which involves adjusting a temporal position of the message window based on the measured message interval. In accordance with certain embodiments, step 614 can involve comparing the measured message interval (e.g., 712 in FIG. 7) to a window positioning interval (e.g., 714 in FIG. 7) indicative of a length of time between when the preceding message was received and a center of the message window. Additionally, step 614 can involve increasing the window positioning interval if the measured message interval was greater than the window positioning interval, and decreasing the window positioning interval if the measured message interval was less than the window positioning interval. If the measured message interval is the same as the window positioning interval, or the same within some specified tolerance (e.g., ±10 ms), then there can be no change to the window positioning interval.

As noted above, a message may be sent by one IMD (e.g., an atrial LP) and received by another IMD (e.g., a ventricular LP), wherein the message is indicative of when the atrial LP sensed an intrinsic atrial depolarization or delivered an atrial pacing pulse. In this, and similar embodiments, the timing of when messages are sent and received will be based on the heart rate of the patient. Adjusting the temporal position of the message window, in accordance with an embodiment described herein, enables the temporal position of the message window to be appropriately adjusted to track increases and decreases in sinus or paced heart rate. In other words, the message window can be adjusted incrementally on each beat to allow for an increasing and decreasing sinus or paced heart rate.

Referring again to FIG. 7, the message window 716 can be thought of as including a first half that extends between a beginning of the message window and a center of the message window, and a second half that extends between the center of the message window and an end of the message window. In certain embodiments, in order to adjust the temporal position of the message window based on the measured message interval, the temporal position of the message window is decreased if the message was received in the first half of the message window, and the temporal position of the message window is increased if the message was received in the second half of the message window.

In accordance with certain embodiments, whenever the window positioning interval is increased it is increased by a fixed increment amount (e.g., 50 ms), and whenever the window positioning interval is decreased, it is decreased by a fixed decrement amount, which may or may not be the same as the fixed increment amount, depending upon implementation. In accordance with other embodiments, whenever the window positioning interval is increased it is increased by a fixed increment percentage (e.g., 5% or 10%), and whenever the window positioning interval is decreased, it is decreased by a fixed decrement percentage, which may or may not be the same as the fixed increment percentage, depending upon implementation. In further embodiments, when the window positioning interval is to be increased (due to the measured message interval being greater than the expected message interval), the window positioning interval is set to be equal to the measured message interval, and when the window positioning interval is to be decreased (due to the measured message interval being less than the expected message interval), the window positioning interval is set to be equal to the measured message interval. In still other embodiments, when the window positioning interval is to be increased (due to the measured message interval being greater than the expected message interval), the window positioning interval is set to be equal to the measured message interval if the measured message interval is within a specified amount (e.g., 50 ms) or a specified percentage (e.g., 10%) of the expected message interval, otherwise the window positioning interval is increased by a fixed increment amount (e.g., 50 ms) or a fixed increment percentage (e.g., 10%). Similarly when the window positioning interval is to be decreased (due to the measured message interval being less than the expected message interval), the window positioning interval is set to be equal to the measured message interval if the measured message interval is within a specified amount (e.g., 50 ms) or a specified percentage (e.g., 10%) of the expected message interval, otherwise the window positioning interval is decreased by a fixed decrement amount (e.g., 50 ms) or a fixed decrement percentage (e.g., 10%). The fixed increment amount or percentage can be the same or different than the fixed decrement amount or percentage, depending upon implementation. In still other embodiments, measured message intervals can be filtered or averaged over time and the temporal position of the message window can be based thereon, e.g., set equal to an average of a plurality of most recently measured message intervals. Other variations are also possible and within embodiments of the present technology.

In accordance with certain embodiments, the window positioning interval (e.g., 714 in FIG. 7) cannot be adjusted to go outside a specified range that defines a minimum window positioning interval and a maximum window positioning interval. This has the effect of keeping the message window within an expected temporal range.

Where a method described with reference to FIGS. 6 and 7 is being used with a dual chamber pacemaker system, such as the one introduced above with reference to FIGS. 1-5, it is possible that the atrial LP detects a premature atrial contraction (PAC) and sends a message indicative thereof to the ventricular LP that would be outside the message window. In accordance with certain embodiments of the present technology, the method is configured such that at least one message sent by an atrial LP, in response to a PAC being detected, is not rejected by a ventricular LP, but causes one or more subsequent messages received by the ventricular LP outside their respective message windows to be rejected. For example, in certain embodiments, determining whether to reject a message can involve determining that the message should be rejected if the message was not received within the message window and M preceding message(s) were also not received within their respective message window(s) (wherein M is a predetermined integer that is ≥1). Such a method can also include determining that the message should not be rejected if the message was received within the message window, and determining that the message should not be rejected if the message was not received within the message window but at least one of the M preceding message(s) was received within its respective message window. If M is set to be equal to 1, then a message corresponding to one PAC would be let through, or more generally, not rejected due to being outside its message window. If M is set to be equal to 2, then two consecutive messages corresponding to two consecutive PACs would be let through, or more generally, not rejected due to being outside their respective message windows.

As noted above, the message window (e.g., 716 in FIG. 7) can have a fixed width. Alternatively, a temporal width of the message window can be adjusted based on a measured message interval. For example, in certain embodiments the message window can be a specified percentage (e.g., 10%) of the most recently measured message window, or a specified percentage (e.g., 10%) of a running average of a plurality of the most recently measured message window.

Figure 6B:
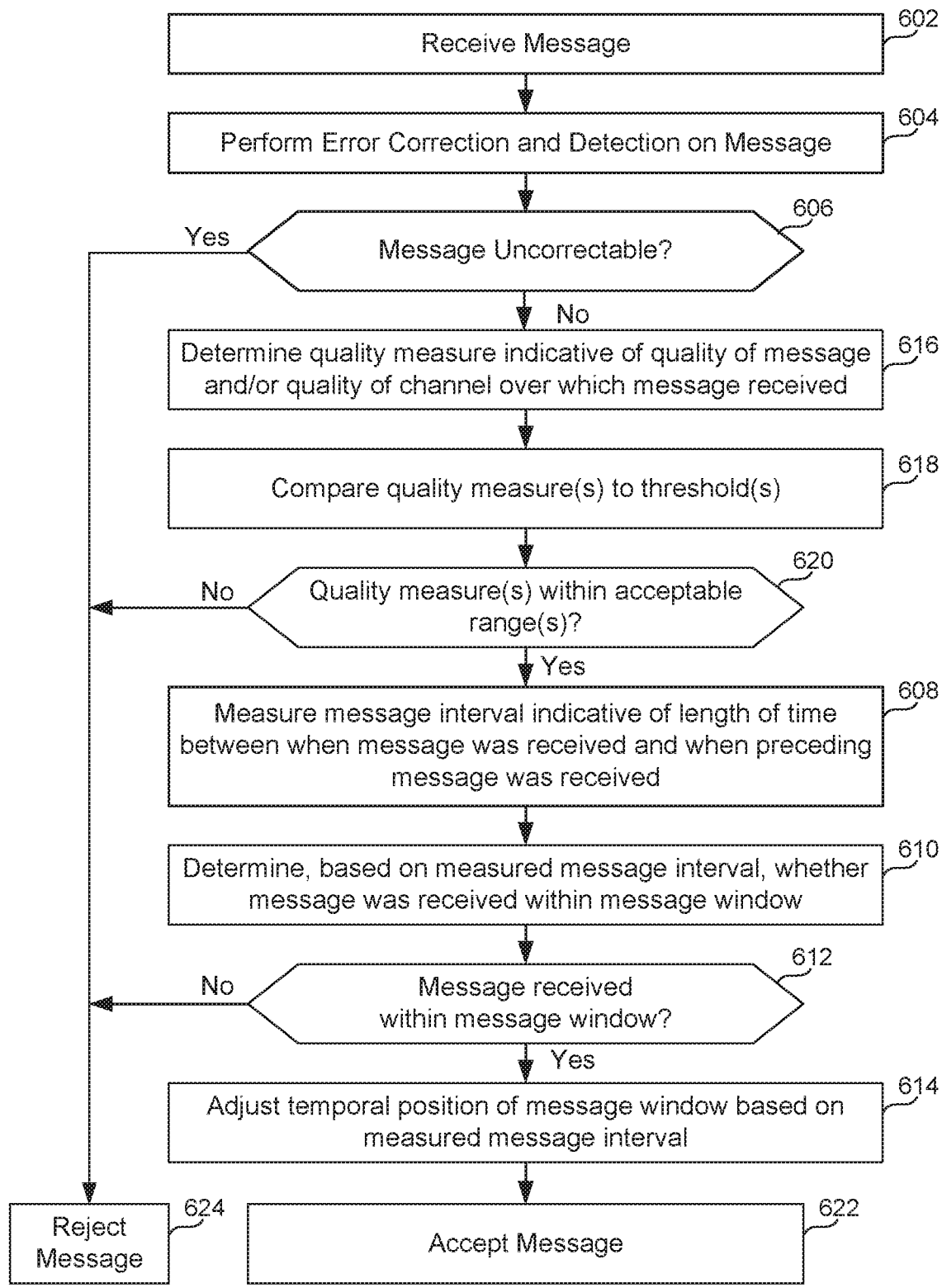
Figure 6C:
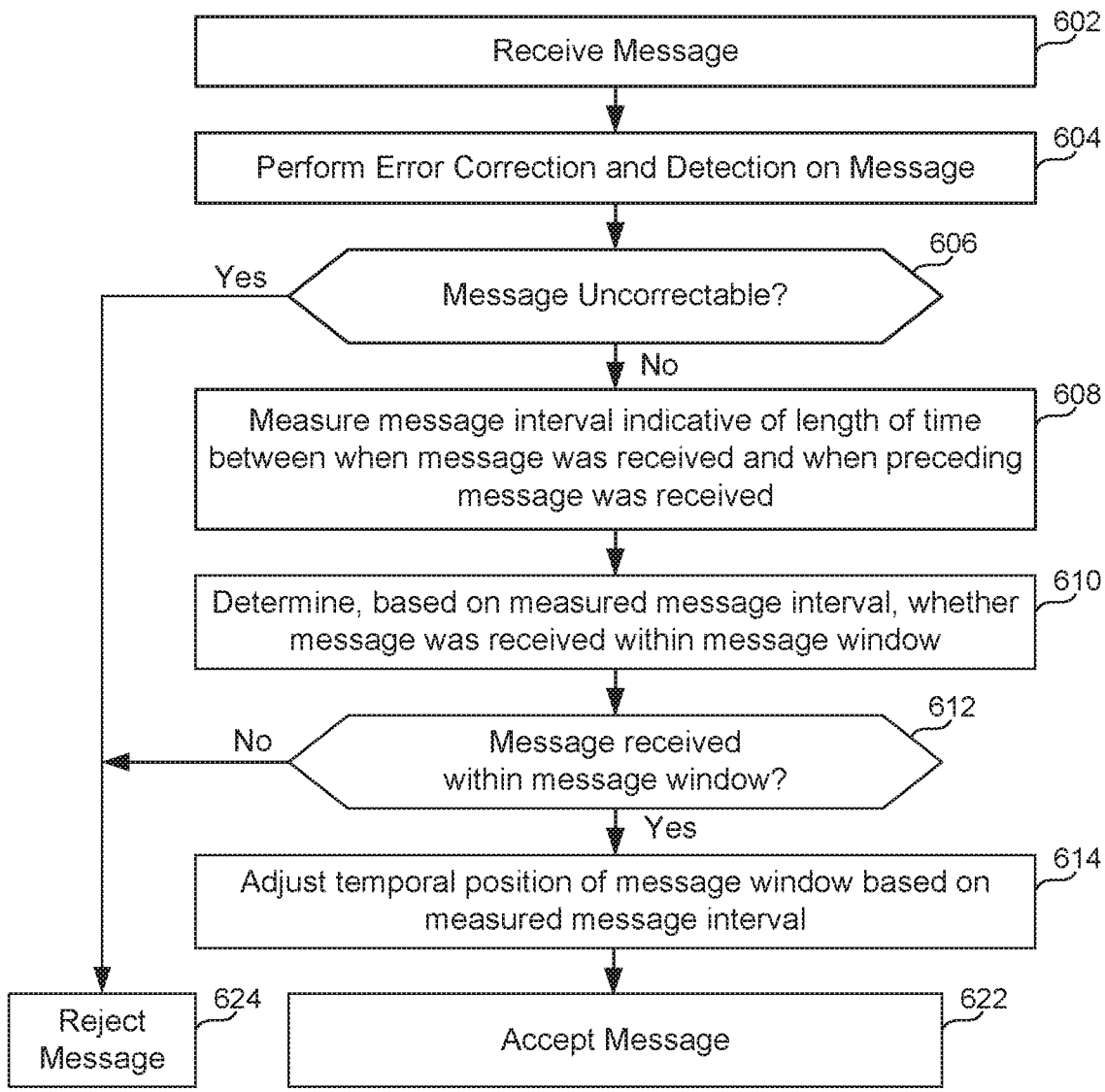

In accordance with certain embodiments, if a message is not uncorrectable (as determined at step 606), and the message is received within the message window (as determined at step 612), then the message will be accepted. In other words, referring to FIG. 6A, in certain embodiments if the answer to the determination at step 612 is YES, then flow can jump from step 614 to step 622 and the message is accepted (e.g., as shown in FIG. 6C). In other embodiments, the quality of the received message and/or the channel over which the message was received is/are also taken into account, to better prevent false messages from being accepted.

More specifically, referring to FIG. 6A, step 616 involves determining one or more quality measure(s) indicative of a quality of the message and/or a quality of a channel over which the message was received. Then, step 618 involves comparing the quality measure(s) to one or more thresholds, in order to determine, at step 620, whether the quality measure(s) are within acceptable range(s). More generally, certain embodiments involve determining whether to reject the message based on one or more quality measure(s). If the answer to the determination at step 620 is NO, then the message is rejected, as indicated at step 624. If the answer to the determination at step 620 is YES, then the message is not rejected, and more specifically, is accepted at step 622. Beneficially, determining whether or not to reject a received message based on message quality and/or the quality of a channel over which the message is received reduces the probability that noise will be mistaken for being a true message, and also reduce the probability of accepting an actual sent message that is received but due to noise it is decoded mistakenly for a different message. More generally, determining whether or not to reject a received message based on message quality and/or the quality of a channel over which the message is received reduces the probability that false messages will be accepted. Additional details of how to perform steps 616, 618 and 620 will be described below.

In FIG. 6A, steps 608 through 614 are shown as being performed prior to steps 616 through 620. In alternative embodiments, steps 616 through 620 are performed prior to steps 608 through 614 (e.g., as shown in FIG. 6B). More generally, determining whether to reject a received message based on whether it is received within its message window can be performed before, or after, determining whether to reject the received message based on its quality and/or the quality of the channel over which the message was received. Other variations are also possible, and within the embodiments described herein.

In accordance with certain embodiments, step 616 involves determining a quality measure indicative of a quality of the message based on results of the error detection and correction performed at step 604. In certain such embodiments, the results of the error detection and correction performed at step 604 specify one of at least two different levels of message quality, which are used to determine such a quality measure. This can involve mapping the results of the error detection and correction to one of at least two different numbers (e.g., to one of the numbers 2, 1 or 0), adjusting an average message quality based on the number, and comparing the average message quality to one or more thresholds. For example, if the message received at step 602 was cleanly received, such that no errors were detected and thus it did not require any correction, then the message may be mapped to the number 2; if the message included an error but was correctable, then the message may be mapped to the number 1; and if the message included an error and was not correctable, then the message may be mapped to the number 0. In other words, in this embodiment, a higher value represents better message quality, and a lower value represents worse message quality. Alternative numbers can be used for the mapping, besides those provided above. For another example, if the message received at step 602 was cleanly received, such that no errors were detected and thus it did not require any correction, then the message may be mapped to the number 5; if the message included an error but was correctable, then the message may be mapped to the number 2; and if the message included an error and was not correctable, then the message may be mapped to the number 0. In certain embodiments, if multiple bits of a message can be corrected, the value to which the message is mapped can be inversely related to the number of bits that required correction, or can be mapped to the negative of the number of bits that required correction. Other variations are also possible and within the scope of embodiments of the present technology.

The average message quality can then be adjusted based on the number to which the message was mapped, e.g., using the equation $Q=(1-1/b)*Q+N*(1/b)$, where Q is the average message quality, N is the number to which the message was mapped, and b is a time constant parameter that controls a rate of change. This equation provides for an exponentially weighted average. Other equations, such as, but not limited to, a simple moving average (e.g., the sum of the message quality of the last M samples, divided by M) can alternatively be used. There are alternative and/or additional ways in which the message quality, or an average thereof, can be determined and used to determine whether a message should be rejected. For example, an amplitude and/or signal strength of a message can be compared to an expected amplitude and/or signal strength range, and the message can be determined to be a false message that should be rejected if the amplitude and/or signal strength is/are outside the expected amplitude and/or signal strength range.

An average message quality or other measure of message quality can be compared to one or more thresholds to determine whether a received message should be rejected. For example, if the measure is above a quality threshold, there may be a determination that the message should not be rejected, and if the measure is below the quality threshold, then there may be a determination that the message should be rejected. To provide hysteresis, more than one threshold may be used, e.g., there can be an upper threshold and a lower threshold. If the measure is above the upper threshold, then there may be a determination that the message should not be rejected, and if the measure is below the lower threshold, then there may be a determination that the message should be rejected. If the measure is between the two thresholds, then whatever was determined for the preceding message can be used for the current message. For example, if the measure is between the upper and lower thresholds, and there was a determination that the preceding message should not be rejected, then there can also be a determination that the current message should not be rejected. On the other hand, if the measure is between the upper and lower thresholds, and there was a determination that the preceding message should be rejected, then there can also be a determination that the current message be rejected. Other variations are also possible.

Additionally, or alternatively, a quality of the channel over which the message was received can also be used to determine whether to reject the received message. For example, noise in the channel over which the message was received can be monitored, and the higher the noise the lower the quality of the channel, and the lower the noise the higher the quality of the channel. For another example, the amplitude of a message signal can be monitored, and the lower the amplitude the lower the quality of the channel, and the higher the amplitude the higher the quality of the channel. For still another example, a wakeup pulse (e.g., 408) of a message can be monitored, and the more it deviates from a specified morphology (e.g., too narrow or too wide), the lower the quality of the channel, and the closer it is to its specified morphology the higher the quality of the channel. The use of alternative and/or additional techniques for determining the quality of the channel over which a message was or can be received can also be used to determine whether to reject or accept a received message. In a similar manner as was discussed above, measures of channel quality can be averaged and compared to one or more thresholds to determine whether a received message should be rejected.

Where various different types of measures are determined at step 616, the various measures may be combined and compared to one or more thresholds. The various measures can be equally weighted, or differently weighted, when combined. Alternatively, each different type of measures can be compared to one or more respective thresholds, and the results thereof can be used to determine whether the received message should be rejected. Depending upon implementation, all results can be equally weighted, or different results can be differently weighted. In accordance with an embodiment, where each of a plurality of different measures of quality are each compared to their own respective threshold(s), then there is a determination that a message should be rejected if at least one of the measures does not satisfy its respective threshold(s). In accordance with another embodiment, where each of a plurality of different measures of quality are each compared to their own respective threshold(s), then there is a determination that a message should be rejected only all of the measures do not satisfy their respective threshold(s). In still another embodiment, there is a determination that a message should be rejected only at least a majority of the measures do not satisfy their respective threshold(s). Other variations are also possible and within the scope of the embodiments described herein.

In FIG. 6A (and FIGS. 6B, 6C and 6D discussed below) if there is a determination that a message is uncorrectable, i.e., if the answer to the determination at step 606 is YES, then flow is shown as going directly to step 624 where the message is rejected. However, even in such a case, the mapping of the results of the error detection and correction to one of at least two different numbers (e.g., to one of the numbers 2, 1 or 0), and the adjusting an average message quality based on the number, e.g., using the equation Q=(1−1/b)*Q+N*(1/b), or some other equation, can still be performed so that Q is appropriately updated to provide a weighted average of message quality over time.

In FIG. 6A (and FIGS. 6B and 6C discussed below), step 614 (which involves adjusting the temporal position of the message window based on the measured message interval) was shown as occurring only if the message was received within the message window, i.e., if the answer to the determination at step 612 is YES. In certain embodiments, even if the answer to the determination at step 612 is NO, step 614 is still performed before the message is rejected at step 624. Such embodiments can be achieved by performing step 614 prior to step 612, e.g., between steps 610 and 612, or between steps 608 and 610. In other words, the temporal position of the window can be adjusted based on the measured message interval regardless of whether a message was received within the message window. This should beneficially prevent situations from occurring where true messages begin to fall outside the message window (e.g., due to sudden changes in an atrial activity) that would make it difficult for the temporal adjustments to the message window to catch up.

Where step 616 involves determining the quality of a channel over which messages are or can be received, step 616 can be triggered in response to a message being received at step 602. Alternatively, step 616 can be performed continually, periodically, or in response to some other triggering event(s), and the most recent results of step 616 can be used whenever a message is received and there is the need to determine whether to accept or reject the received message.

In alternative embodiments, the order of the steps shown in and described with reference to FIG. 6A are rearranged. In other words, embodiments of the present technology are not limited to the order in which the steps described with reference to FIG. 6A are performed. For example, in accordance with certain embodiments, step 616, 618 and 620 are performed prior steps 608, 610, 612 and 614, as shown in FIG. 6B. Other variations are also possible and within the scope of the embodiments described herein. For an example, the order of steps 614 and 622 shown in FIG. 6B can be swapped. Further, as already noted above, step 614 can be performed prior to step 612, e.g., between steps 610 and 612, or between steps 608 and 610.

In the embodiments summarized with reference to FIGS. 6A and 6B, determinations of whether to reject a received message may be based on both the timing of when a message was received relative to one or more preceding messages, as well one or more measures of quality, which as explained above, can relate to message quality and/or quality of the channel over which a message was received.

In accordance with other embodiments, determinations of whether to reject a received message are based on the timing of when a message was received relative to one or more preceding messages, without being based on any measures message quality and/or quality of the channel over which a message was received. An example of such an embodiment is shown, for example, in FIG. 6C. A comparison between FIG. 6C and FIGS. 6A and 6B shows that FIG. 6C does not include steps 616, 618 and 620.

In accordance with further embodiments, determinations of whether to reject a received message are based on measures of message quality and/or quality of the channel over which a message was received, without being based on the timing of when the message was received relative to one or more preceding messages. An example of such an embodiment is shown, for example, in FIG. 6D. A comparison between FIG. 6D and FIGS. 6A and 6B shows that FIG. 6D does not include steps 608, 610, 612 and 614.

Figure 6D:
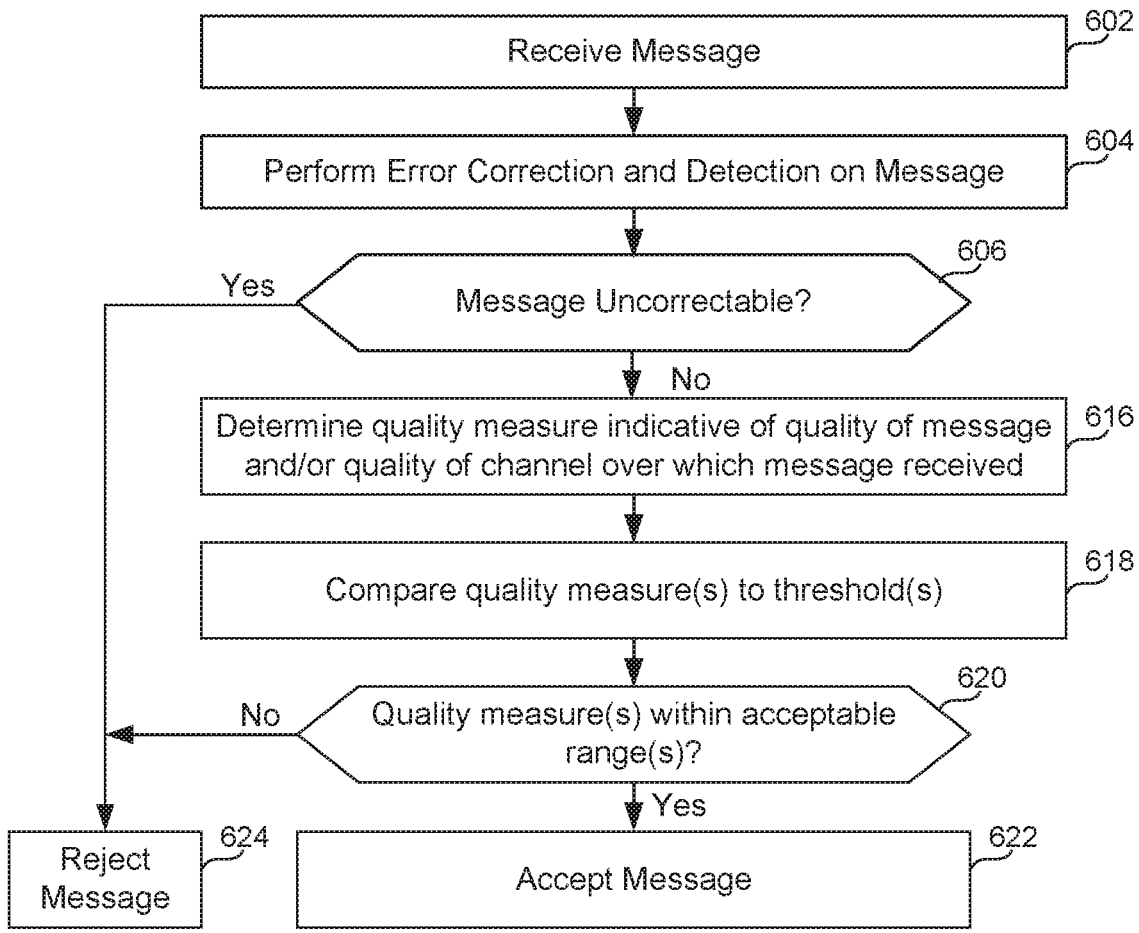

A reason for using one of the embodiments of FIG. 6C or 6D instead of one of the embodiments of FIG. 6A or 6B is that they would likely be more simple and easier to implement in an IMD, especially in a rather small IMD such as an LP. A reason for using one of the embodiments of FIG. 6A or 6B instead of one of the embodiments of FIG. 6C or 6D is that the embodiments of FIG. 6A or 6B should reject more false messages than the embodiments of FIG. 6C or 6D, since the embodiments of FIGS. 6A and 6B scrutinize received messages to a greater extent than the embodiments of FIGS. 6C and 6D. A reason for using the embodiment of FIG. 6D instead of the embodiment of FIG. 6C is that the embodiment of FIG. 6C would likely be more simple and easier to implement in an IMD, especially a rather small IMD such as an LP.

Figure 8:
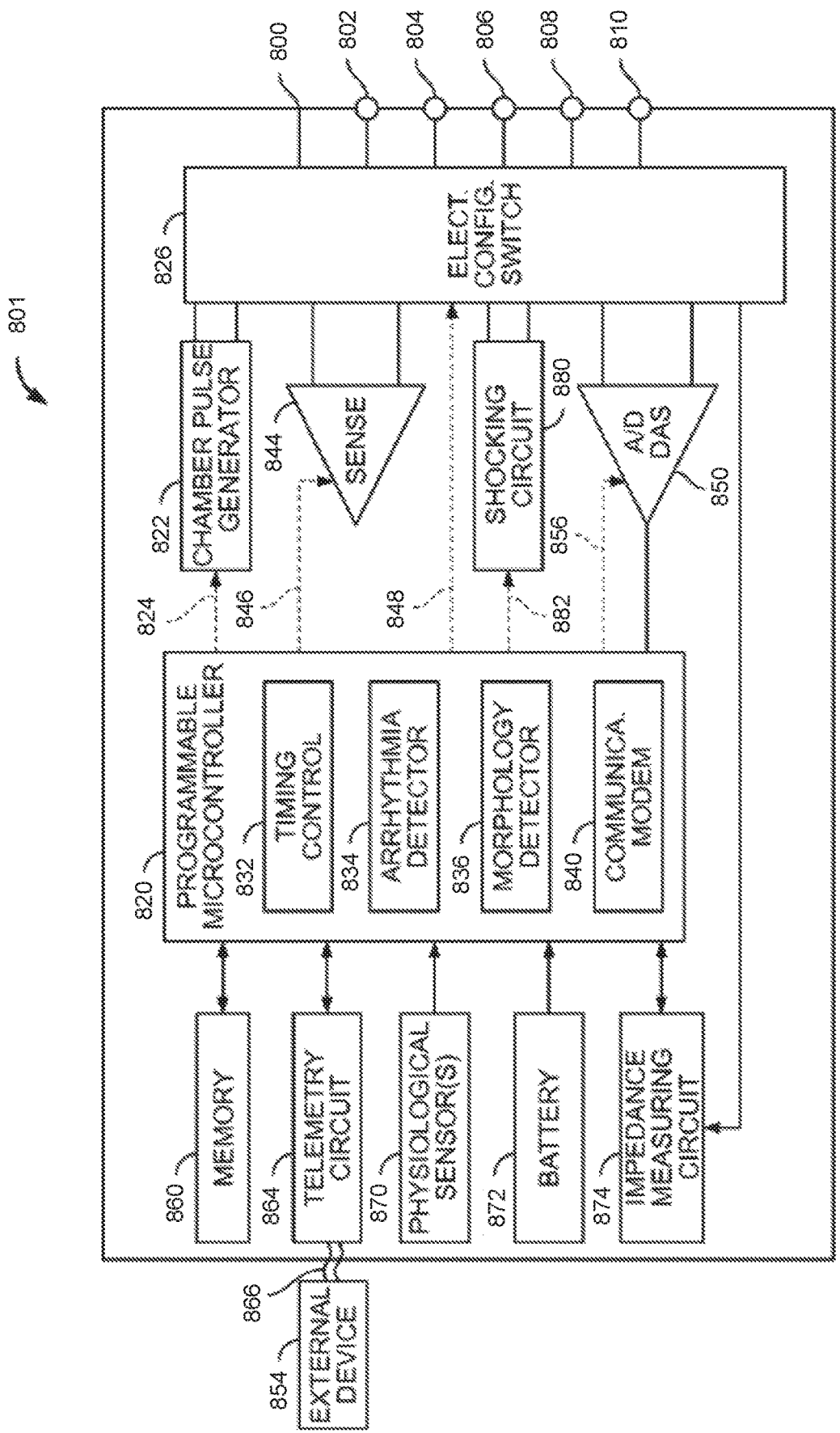
FIG. 8 shows a block diagram of one embodiment of an LP that is implanted into the patient as part of the implantable cardiac system in accordance with certain embodiments herein.

FIG. 8 shows a block diagram of one embodiment of an LP 801 that is implanted into the patient as part of the implantable cardiac system in accordance with certain embodiments herein. LP 801 may be implemented as a full-function biventricular pacemaker, equipped with both atrial and ventricular sensing and pacing circuitry for four chamber sensing and stimulation therapy (including both pacing and shock treatment). Optionally, LP 801 may provide full-function cardiac resynchronization therapy. Alternatively, LP 801 may be implemented with a reduced set of functions and components. For instance, the IMD may be implemented without ventricular sensing and pacing.

LP 801 has a housing 800 to hold the electronic/computing components. Housing 800 (which is often referred to as the "can", "case", "encasing", or "case electrode") may be programmably selected to act as the return electrode for certain stimulus modes. Housing 800 may further include a connector (not shown) with a plurality of terminals 802, 804, 806, 808, and 810. The terminals may be connected to electrodes that are located in various locations on housing 800 or elsewhere within and about the heart. LP 801 includes a programmable microcontroller 820 that controls various operations of LP 801, including cardiac monitoring and stimulation therapy. Microcontroller 820 includes a microprocessor (or equivalent control circuitry), RAM and/or ROM memory, logic and timing circuitry, state machine circuitry, and I/O circuitry.

LP 801 further includes a first pulse generator 822 that generates stimulation pulses for delivery by one or more electrodes coupled thereto. Pulse generator 822 is controlled by microcontroller 820 via control signal 824. Pulse generator 822 may be coupled to the select electrode(s) via an electrode configuration switch 826, which includes multiple switches for connecting the desired electrodes to the appropriate I/O circuits, thereby facilitating electrode programmability. Switch 826 is controlled by a control signal 828 from microcontroller 820.

In the embodiment of FIG. 8, a single pulse generator 822 is illustrated. Optionally, the IMD may include multiple pulse generators, similar to pulse generator 822, where each pulse generator is coupled to one or more electrodes and controlled by microcontroller 820 to deliver select stimulus pulse(s) to the corresponding one or more electrodes.

Microcontroller 820 is illustrated as including timing control circuitry 832 to control the timing of the stimulation pulses (e.g., pacing rate, atrio-ventricular (AV) delay, atrial interconduction (A-A) delay, or ventricular interconduction (V-V) delay, etc.). Timing control circuitry 832 may also be used for the timing of refractory periods, blanking intervals, noise detection windows, evoked response windows, alert intervals, marker channel timing, and so on. Microcontroller 820 also has an arrhythmia detector 834 for detecting arrhythmia conditions and a morphology detector 836. Although not shown, the microcontroller 820 may further include other dedicated circuitry and/or firmware/software components that assist in monitoring various conditions of the patient's heart and managing pacing therapies.

LP 801 is further equipped with a communication modem (modulator/demodulator) 840 to enable wireless communication with the remote slave pacing unit. Modem 840 may include one or more transmitters and two or more receivers as discussed herein in connection with FIG. 1B. In one implementation, modem 840 may use low or high frequency modulation. As one example, modem 840 may transmit i2i messages and other signals through conductive communication between a pair of electrodes. Modem 840 may be implemented in hardware as part of microcontroller 820, or as software/firmware instructions programmed into and executed by microcontroller 820. Alternatively, modem 840 may reside separately from the microcontroller as a stand-alone component.

LP 801 includes a sensing circuit 844 selectively coupled to one or more electrodes, that perform sensing operations, through switch 826 to detect the presence of cardiac activity in the right chambers of the heart. Sensing circuit 844 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit to sense low amplitude signal characteristics of atrial fibrillation. Switch 826 determines the sensing polarity of the cardiac signal by selectively closing the appropriate switches. In this way, the clinician may program the sensing polarity independent of the stimulation polarity.

The output of sensing circuit 844 is connected to microcontroller 820 which, in turn, triggers or inhibits the pulse generator 822 in response to the presence or absence of cardiac activity. Sensing circuit 844 receives a control signal 846 from microcontroller 820 for purposes of controlling the gain, threshold, polarization charge removal circuitry (not shown), and the timing of any blocking circuitry (not shown) coupled to the inputs of the sensing circuitry.

In the embodiment of FIG. 8, a single sensing circuit 844 is illustrated. Optionally, the IMD may include multiple sensing circuits, similar to sensing circuit 844, where each sensing circuit is coupled to one or more electrodes and controlled by microcontroller 820 to sense electrical activity detected at the corresponding one or more electrodes. Sensing circuit 844 may operate in a unipolar sensing configuration or in a bipolar sensing configuration.

LP 801 further includes an analog-to-digital (A/D) data acquisition system (DAS) 850 coupled to one or more electrodes via switch 826 to sample cardiac signals across any pair of desired electrodes. Data acquisition system 850 is configured to acquire intracardiac electrogram signals, convert the raw analog data into digital data, and store the digital data for later processing and/or telemetric transmission to an external device 854 (e.g., a programmer, local transceiver, or a diagnostic system analyzer). Data acquisition system 850 is controlled by a control signal 856 from the microcontroller 820.

Microcontroller 820 is coupled to a memory 860 by a suitable data/address bus. The programmable operating parameters used by microcontroller 820 are stored in memory 860 and used to customize the operation of LP 801 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy.

The operating parameters of LP 801 may be non-invasively programmed into memory 860 through a telemetry circuit 864 in telemetric communication via communication link 866 with external device 854. Telemetry circuit 864 allows intracardiac electrograms and status information relating to the operation of LP 801 (as contained in microcontroller 820 or memory 860) to be sent to external device 854 through communication link 866.

LP 801 can further include magnet detection circuitry (not shown), coupled to microcontroller 820, to detect when a magnet is placed over the unit. A magnet may be used by a clinician to perform various test functions of LP 801 and/or to signal microcontroller 820 that external device 854 is in place to receive or transmit data to microcontroller 820 through telemetry circuits 864.

LP 801 can further include one or more physiological sensors 870. Such sensors are commonly referred to as "rate-responsive" sensors because they are typically used to adjust pacing stimulation rates according to the exercise state of the patient. However, physiological sensor 870 may further be used to detect changes in cardiac output, changes in the physiological condition of the heart, or diurnal changes in activity (e.g., detecting sleep and wake states). Signals generated by physiological sensors 870 are passed to microcontroller 820 for analysis. Microcontroller 820 responds by adjusting the various pacing parameters (such as rate, AV Delay, V-V Delay, etc.) at which the atrial and ventricular pacing pulses are administered. While shown as being included within LP 801, physiological sensor(s) 870 may be external to LP 801, yet still be implanted within or carried by the patient. Examples of physiologic sensors might include sensors that, for example, sense respiration rate, pH of blood, ventricular gradient, activity, position/posture, minute ventilation (MV), and so forth.

A battery 872 provides operating power to all of the components in LP 801. Battery 872 is capable of operating at low current drains for long periods of time, and is capable of providing high-current pulses (for capacitor charging) when the patient requires a shock pulse (e.g., in excess of 2 A, at voltages above 2 V, for periods of 10 seconds or more). Battery 872 also desirably has a predictable discharge characteristic so that elective replacement time can be detected. As one example, LP 801 employs lithium/silver vanadium oxide batteries.

LP 801 further includes an impedance measuring circuit 874, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. Impedance measuring circuit 874 is coupled to switch 826 so that any desired electrode may be used. In this embodiment LP 801 further includes a shocking circuit 880 coupled to microcontroller 820 by a data/address bus 882.

In some embodiments, the LPs 102 and 104 are configured to be implantable in any chamber of the heart, namely either atrium (RA, LA) or either ventricle (RV, LV). Furthermore, for dual-chamber configurations, multiple LPs may be co-implanted (e.g., one in the RA and one in the RV, one in the RV and one in the coronary sinus proximate the LV). Certain pacemaker parameters and functions depend on (or assume) knowledge of the chamber in which the pacemaker is implanted (and thus with which the LP is interacting; e.g., pacing and/or sensing). Some non-limiting examples include: sensing sensitivity, an evoked response algorithm, use of AF suppression in a local chamber, blanking & refractory periods, etc. Accordingly, each LP needs to know an identity of the chamber in which the LP is implanted, and processes may be implemented to automatically identify a local chamber associated with each LP.

Processes for chamber identification may also be applied to subcutaneous pacemakers, ICDs, with leads and the like. A device with one or more implanted leads, identification and/or confirmation of the chamber into which the lead was implanted could be useful in several pertinent scenarios. For example, for a DR or CRT device, automatic identification and confirmation could mitigate against the possibility of the clinician inadvertently placing the V lead into the A port of the implantable medical device, and vice-versa. As another example, for an SR device, automatic identification of implanted chamber could enable the device and/or programmer to select and present the proper subset of pacing modes (e.g., AAI or VVI), and for the IPG to utilize the proper set of settings and algorithms (e.g., V-AutoCapture vs ACap-Confirm, sensing sensitivities, etc.).

While many of the embodiments of the present technology described above have been described as being for use with LP type IMDs, embodiments of the present technology that are for use in reducing how often a first receiver of an IMD wakes up a second receiver of an IMD, in order to reduce power consumption, can also be used with other types of IMDs besides an LP. Accordingly, unless specifically limited to use with an LP, the claims should not be limited to use with LP type IMDs.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments of the present technology without departing from its scope. While the dimensions, types of materials and coatings described herein are intended to define the parameters of the embodiments of the present technology, they are by no means limiting and are exemplary embodiments. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. For use by an implantable medical device (IMD) configured to communicate with a further IMD, a method for reducing how often the IMD accepts false messages from the further IMD, the method comprising:
   receiving a message from the further IMD;
   performing error detection and correction on the message;
   determining, based on results of the error detection and correction, a quality measure indicative of at least one of a quality of the message or a quality of a channel over which the message was received; and
   determining whether to reject the message based on the quality measure;

wherein the message, if accepted, is used by the IMD to at least one of trigger a timer or trigger an event.

2. The method of claim 1, wherein the quality measure is indicative of the quality of the message, and the results of the error detection and correction specify one of at least two different levels of message quality, and further comprising:
mapping the results of the error detection and correction to one number of at least two different numbers;
adjusting an average message quality based on the number to which the results of the error detection and correction is mapped; and
comparing the average message quality to one or more thresholds;
wherein the determining whether to reject the message based on the quality measure comprises determining whether to reject the message based on results of the comparing the average message quality to the one or more thresholds.

3. The method of claim 2, wherein the mapping the results of the error detection and correction to one number of at least two different numbers includes:
mapping the results of the error detection and correction to a first number if the results indicated the message was cleanly received without any correcting being needed;
mapping the results of the error detection and correction to a second number that is less than the first number if the results indicated the message was corrected; and
mapping the results of the error detection and correction to a third number that is less than the second number if the results indicated the message was uncorrectable.

4. The method of claim 3, wherein the adjusting the average message quality based on the number is performed using an equation $Q=(1-1/b)*Q+N*(1/b)$, where Q is the average message quality, N is the number to which the results of the error detection and correction was mapped, and b is a time constant parameter that controls a rate of change.

5. The method of claim 2, wherein the determining whether to reject the message comprises:
determining that the message should be rejected if the average message quality is below a corresponding lower threshold;
determining that the message should not be rejected if the average message quality is above a corresponding upper threshold; and
if the average message quality is between the corresponding lower and upper thresholds, then determining that the message should be rejected if the preceding message was rejected, and determining that the message should not be rejected if the preceding message was not rejected.

6. The method of claim 1, wherein the determining whether to reject the message comprises:
determining that the message should be rejected if the quality measure is below a corresponding lower threshold;
determining that the message should not be rejected if the quality measure is above a corresponding upper threshold; and
if the quality measure is between the corresponding lower and upper thresholds, then determining that the message should be rejected if the preceding message was rejected, and determining that the message should not be rejected if the preceding message was not rejected.

7. The method of claim 1, wherein the quality measure is based on at least one of:
whether an amplitude or power of a received signal including the message is within an expected amplitude or power range; or
whether a timing of the message is within an expected timing range.

8. The method of claim 1, wherein the quality measure is indicative of the quality of the channel over which the message was received.

9. The method of claim 8, further comprising:
measuring noise associated with the channel over which the message was received; and
determining the quality of the channel over which the message was received based on the measured noise associated with the channel.

10. An implantable medical device (IMD), comprising:
at least one receiver configured to receive messages from a further IMD;
at least one of a processor or controller configured to:
perform error detection and correction on a message received by the at least one receiver;
determine a quality measure indicative of at least one of a quality of the message or a quality of a channel over which the message was received; and
determine whether to reject the message based on the quality measure;
wherein the message, if accepted, is used by the IMD to at least one of trigger a timer or trigger an event.

11. The IMD of claim 10, wherein the quality measure is indicative of the quality of the message, the results of the error detection and correction specify one of at least two different levels of message quality, and the at least one of a processor or controller is configured to:
map the results of the error detection and correction to one number of at least two different numbers;
adjust an average message quality based on the number;
compare the average message quality to one or more thresholds; and
determine whether to reject the message based on results of the comparing the average message quality to the one or more thresholds.

12. The IMD of claim 11, wherein the at least one of a processor or controller is configured to:
map the results of the error detection and correction to a first number if the results indicated the message was cleanly received without any correcting being needed;
map the results of the error detection and correction to a second number that is less than the first number if the results indicated the message was corrected; and
map the results of the error detection and correction to a third number that is less than the second number if the results indicated the message was uncorrectable.

13. The IMD of claim 12, wherein the at least one of a processor or controller is configured to adjust the average message quality based on the number using an equation $Q=(1-1/b)*Q+N*(1/b)$, where Q is the average message quality, N is the number to which the results of the error detection and correction was mapped, and b is a time constant parameter that controls a rate of change.

14. The IMD of claim 11, wherein the at least one of a processor or controller is configured to:
determine that the message should be rejected if the average message quality is below a corresponding lower threshold;
determine that the message should not be rejected if the average message quality is above a corresponding upper threshold; and if the average message quality is between the corresponding lower and upper thresholds, then determine that the message should be rejected if the preceding message was rejected, and determine that the message should not be rejected if the preceding message was not rejected.

15. The IMD of claim 10, wherein the at least one of a processor or controller is configured to:
   determine that the message should be rejected if the quality measure is below a corresponding lower threshold;
   determine that the message should not be rejected if the quality measure is above a corresponding upper threshold; and
   if the quality measure is between the corresponding lower and upper thresholds, then determine that the message should be rejected if the preceding message was rejected, and determine that the message should not be rejected if the preceding message was not rejected.

16. The IMD of claim 10, wherein the at least one of a processor or controller is configured to determine the quality measure based on at least one of:
   whether an amplitude or power of a received signal including the message is within an expected amplitude or power range; or
   whether a timing of the message is within an expected timing range.

17. The IMD of claim 10, wherein the quality measure is indicative of the quality of the channel over which the message was received.

18. The IMD of claim 17, wherein at least one of the at least one receiver or the at least one of a processor or controller is configured to measure noise associated with the channel over which the message was received, and the at least one of a processor or controller is configured to determine the quality of the channel over which the message was received based on the measured noise associated with the channel.

19. An implantable medical device (IMD), comprising:
   at least one receiver configured to receive messages from a further IMD;
   at least one of a processor or controller configure to:
      perform error detection and correction on a message received by the at least one receiver;
      determine whether the message was received within a message window, if the message is not uncorrectable;
      accept the message, if the message is not uncorrectable and is received within the message window; and
      reject the message, if the message is uncorrectable, or if the message is not received within the message window;
   wherein the message, if accepted, is used by the IMD to at least one of trigger a timer or trigger an event.

20. The IMD of claim 19, wherein the at least one of a processor or controller configure to:
   measure a message interval indicative of a length of time between when the message was received and when a preceding message was received;
   determine, based on the measured message interval, whether the message was received within the message window; and
   adjust a temporal position of the message window based on the measured message interval, if the message was received within the message window.

* * * * *